(12) United States Patent
Crnkovich et al.

(10) Patent No.: US 8,110,104 B2
(45) Date of Patent: Feb. 7, 2012

(54) DIALYSIS SYSTEMS AND RELATED COMPONENTS

(75) Inventors: Martin Joseph Crnkovich, Walnut Creek, CA (US); Lynn E. Jensen, Syracuse, UT (US); Melvin D. Jensen, West Haven, UT (US); Deloy Lindley, North Ogden, UT (US); Mohsen Reihanifam, Rancho Sante Fe, CA (US); Colin Weaver, Pleasanton, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 560 days.

(21) Appl. No.: 12/234,186

(22) Filed: Sep. 19, 2008

(65) Prior Publication Data

US 2009/0101566 A1  Apr. 23, 2009

Related U.S. Application Data

(60) Provisional application No. 60/973,734, filed on Sep. 19, 2007.

(51) Int. Cl.
*B01D 61/30* (2006.01)

(52) U.S. Cl. ............. 210/321.6; 210/541; 210/646; 604/5.01; 604/29; 604/65; 285/18; 285/120.1; 137/343

(58) Field of Classification Search ............ 210/321.6, 210/321.65, 321.71, 541, 542, 645, 646; 604/4.01, 5.01, 6.01, 29, 65; 285/18, 120.1; 137/343
See application file for complete search history.

(56) References Cited

U.S. PATENT DOCUMENTS

| | | | |
|---|---|---|---|
| 3,946,731 A | 3/1976 | Lichtenstein | |
| 3,985,135 A | 10/1976 | Carpenter et al. | |
| 4,026,669 A | 5/1977 | Leonard et al. | |
| 4,187,057 A * | 2/1980 | Xanthopoulos | 417/63 |
| 4,370,983 A | 2/1983 | Lichtenstein | |
| 4,643,713 A | 2/1987 | Viitala | |
| 4,662,906 A | 5/1987 | Matkovich et al. | |
| 4,702,675 A | 10/1987 | Aldrovandi et al. | |
| 4,997,464 A | 3/1991 | Kopf | |
| 5,061,236 A | 10/1991 | Sutherland et al. | |
| 5,330,425 A | 7/1994 | Utterberg | |
| 5,425,173 A * | 6/1995 | Moss et al. | 29/888.021 |
| 5,441,636 A | 8/1995 | Chevallet et al. | |
| 5,460,490 A * | 10/1995 | Carr et al. | 417/44.2 |
| 5,578,070 A | 11/1996 | Utterberg | |
| 5,614,677 A | 3/1997 | Wamsiedler et al. | |
| 5,643,205 A | 7/1997 | Utterberg | |
| 5,788,671 A * | 8/1998 | Johnson | 604/131 |
| 5,849,065 A | 12/1998 | Wojke | |

(Continued)

FOREIGN PATENT DOCUMENTS

EP  0458041  11/1991

(Continued)

OTHER PUBLICATIONS

Gambre®, "DEHP-Free Cartridge Blood Sets", © Nov. 2004, Gambro, Inc, Lakewood, CO, 4 pp.

(Continued)

*Primary Examiner* — Joseph Drodge
(74) *Attorney, Agent, or Firm* — Fish & Richardson P.C.

(57) ABSTRACT

A cassette is described for holding circuit components used with a hemodialysis machine.

48 Claims, 20 Drawing Sheets

U.S. PATENT DOCUMENTS

| | | | |
|---|---|---|---|
| 5,928,177 A | | 7/1999 | Brugger et al. |
| 5,938,634 A | * | 8/1999 | Packard .................... 604/29 |
| 5,989,423 A | * | 11/1999 | Kamen et al. ............. 210/258 |
| 6,179,801 B1 | | 1/2001 | Holmes et al. |
| 6,196,987 B1 | | 3/2001 | Holmes et al. |
| 6,200,287 B1 | | 3/2001 | Keller et al. |
| 6,231,537 B1 | | 5/2001 | Holmes et al. |
| 6,234,989 B1 | | 5/2001 | Brierton et al. |
| 6,280,406 B1 | | 8/2001 | Dolecek et al. |
| 6,337,049 B1 | | 1/2002 | Tamari |
| 6,361,518 B1 | | 3/2002 | Brierton et al. |
| 6,409,696 B1 | | 6/2002 | Toavs et al. |
| 6,497,674 B1 | | 12/2002 | Steele et al. |
| 6,514,225 B1 | | 2/2003 | Utterberg et al. |
| 6,695,803 B1 | | 2/2004 | Robinson et al. |
| 6,725,726 B1 | | 4/2004 | Adolfs et al. |
| 6,730,055 B2 | | 5/2004 | Bainbridge et al. |
| 6,743,201 B1 | * | 6/2004 | Donig et al. .................. 604/114 |
| 6,755,801 B2 | | 6/2004 | Utterberg et al. |
| 6,764,460 B2 | * | 7/2004 | Dolecek et al. ............. 604/6.01 |
| 6,790,195 B2 | | 9/2004 | Steele et al. |
| 6,852,090 B2 | | 2/2005 | Burbank et al. |
| 6,887,214 B1 | | 5/2005 | Levin et al. |
| 7,021,148 B2 | | 4/2006 | Kuhn et al. |
| 7,115,107 B2 | | 10/2006 | Delnevo et al. |
| 7,238,164 B2 | * | 7/2007 | Childers et al. ............. 604/6.11 |
| 7,476,209 B2 | * | 1/2009 | Gara et al. .................... 604/6.01 |
| 7,517,387 B2 | | 4/2009 | Chevallet et al. |
| 2002/0014462 A1 | * | 2/2002 | Muller ........................ 210/745 |
| 2002/0072718 A1 | | 6/2002 | Brugger et al. |
| 2004/0238416 A1 | | 12/2004 | Burbank et al. |
| 2005/0054968 A1 | | 3/2005 | Giannella |
| 2005/0131332 A1 | * | 6/2005 | Kelly et al. ................... 604/4.01 |
| 2005/0230292 A1 | | 10/2005 | Beden et al. |
| 2007/0106198 A1 | * | 5/2007 | Folden et al. ................ 604/6.14 |
| 2007/0193940 A1 | | 8/2007 | Duchamp et al. |
| 2007/0269340 A1 | | 11/2007 | Dannenmaier et al. |
| 2010/0222735 A1 | * | 9/2010 | Plahey et al. ................ 604/29 |

FOREIGN PATENT DOCUMENTS

| | | |
|---|---|---|
| EP | 0728509 | 8/1996 |
| EP | 0887100 | 12/1998 |
| EP | 1529545 | 5/2005 |
| WO | WO 96/40322 | 12/1996 |
| WO | WO 9702056 | 1/1997 |
| WO | WO 0108722 | 2/2001 |
| WO | WO 0164312 | 9/2001 |
| WO | WO 2005/044341 | 5/2005 |
| WO | WO 2005077490 | 8/2005 |

OTHER PUBLICATIONS

Gambro®, "Prisma® 1000," For Increased Filtration Capacity, © Aug. 2001, Gambro Renal Products, Inc., Lakewood, CO, 2 pp.

Gambro®, "Prisma® M60 and M100 Pre-Pump Infusion Sets—Introducing: The unique solution that enables Physicians to choose a predilution method that meets the needs of their patients", © 2004, Gambro Inc., Lakewood, CO, 4 pp.

Gambro®, "Prismaflex ™, Anticipating Critical Care needs and taking our innovative response . . . to new heights", © 2004, Gambro Inc., Lakewood, CO, 8 pp.

Manns, Markus et al., "The acu-men: A new device for continuous renal replacement therapy in acute renal failure," Kidney International, vol. 54, pp. 208-274, 1998.

International Search Report and Written Opinion; PCT/US2008/076995; mailed Mar. 24, 2009.

Acu•men, Acute Dialysis Machine Operating Instructions, Software Version 1.0, Fresenius MT acu•men, 1/05.96 (OP), 146 pages. , anonymous.

\* cited by examiner

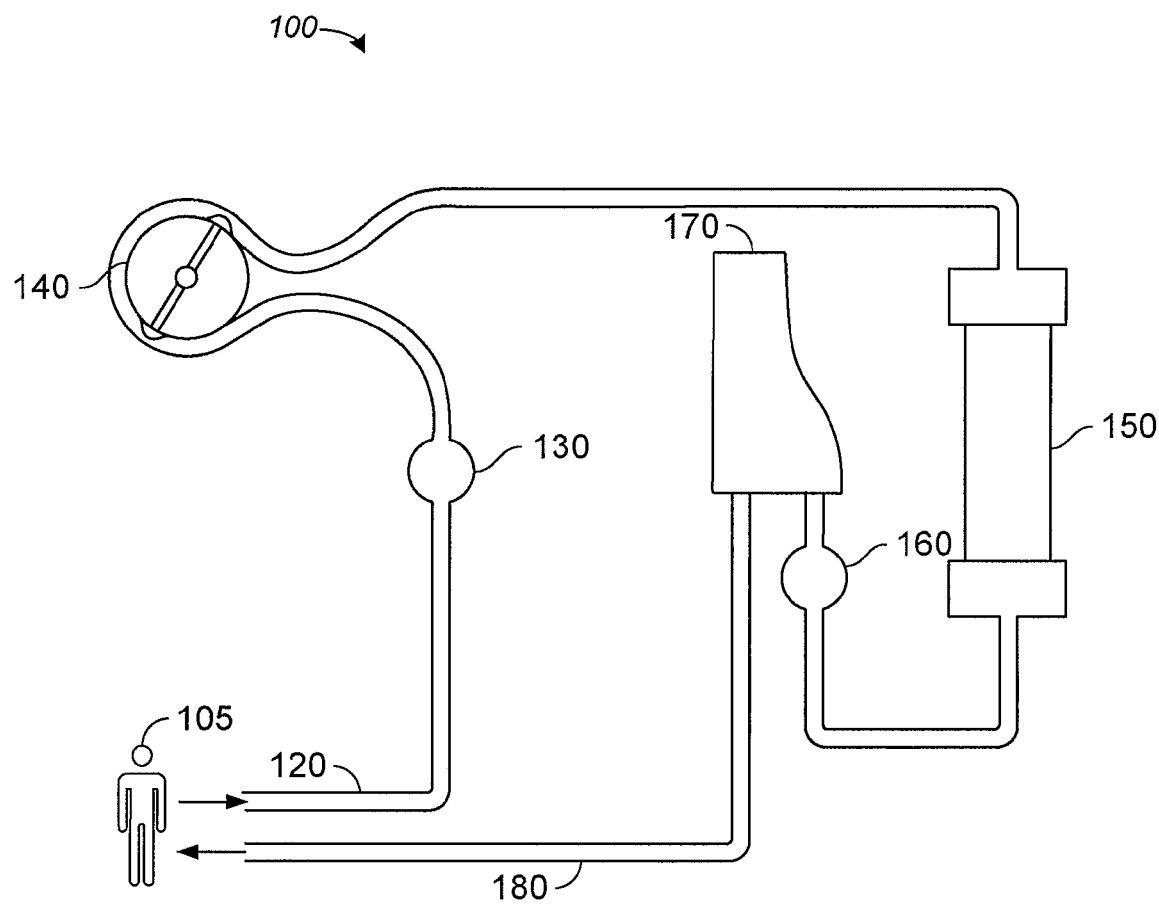
FIG._1

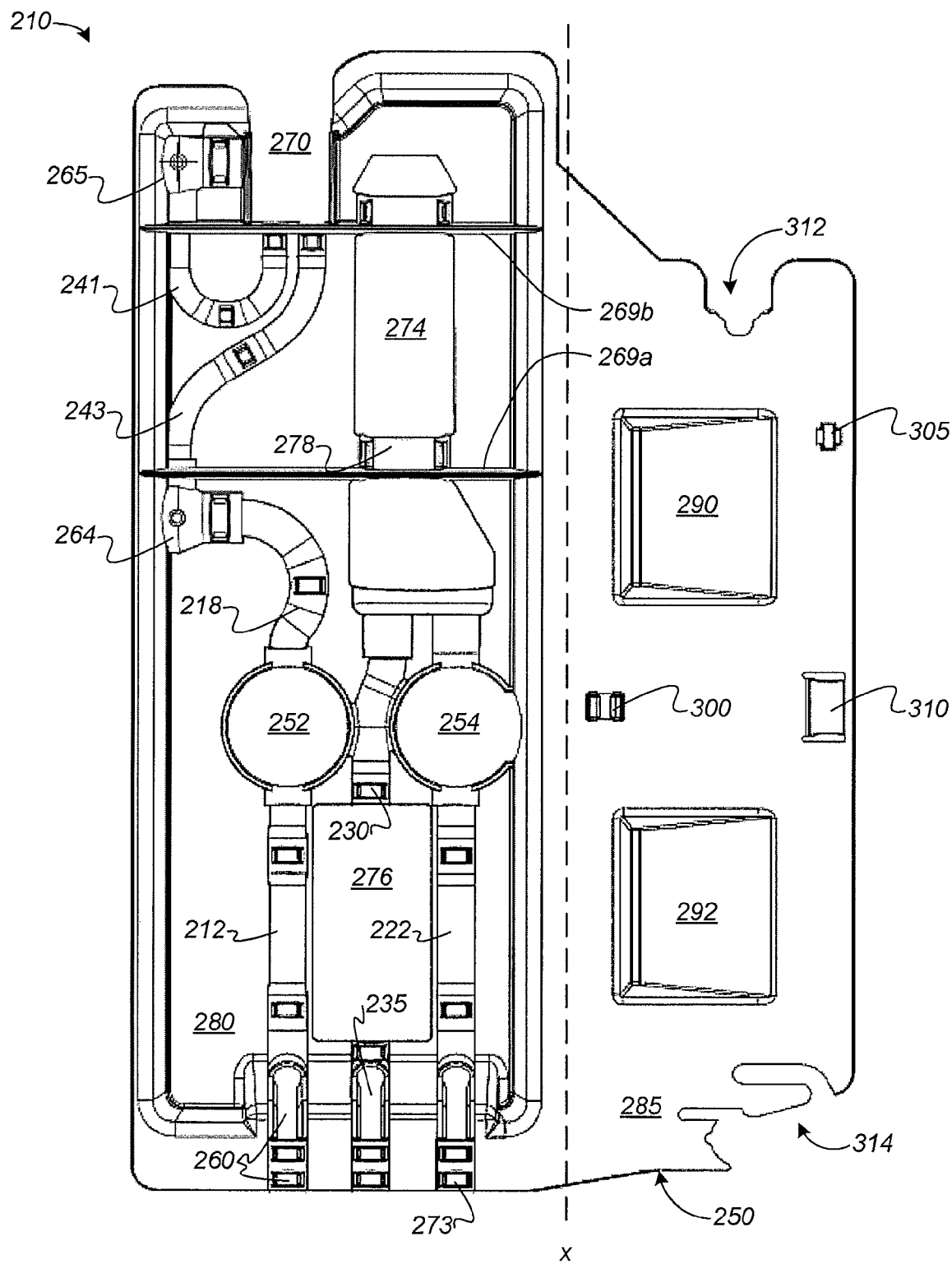
FIG._2

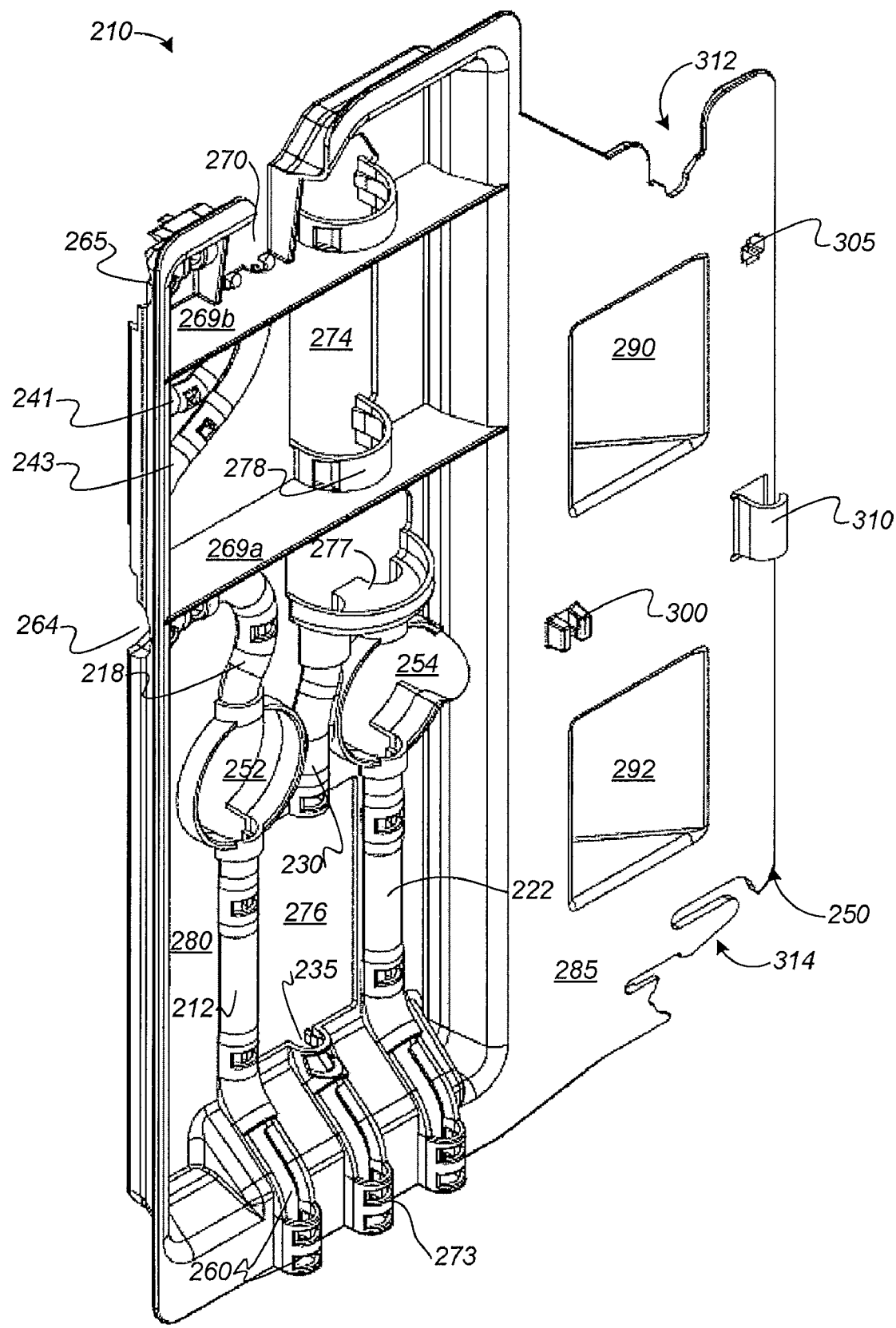
FIG._3

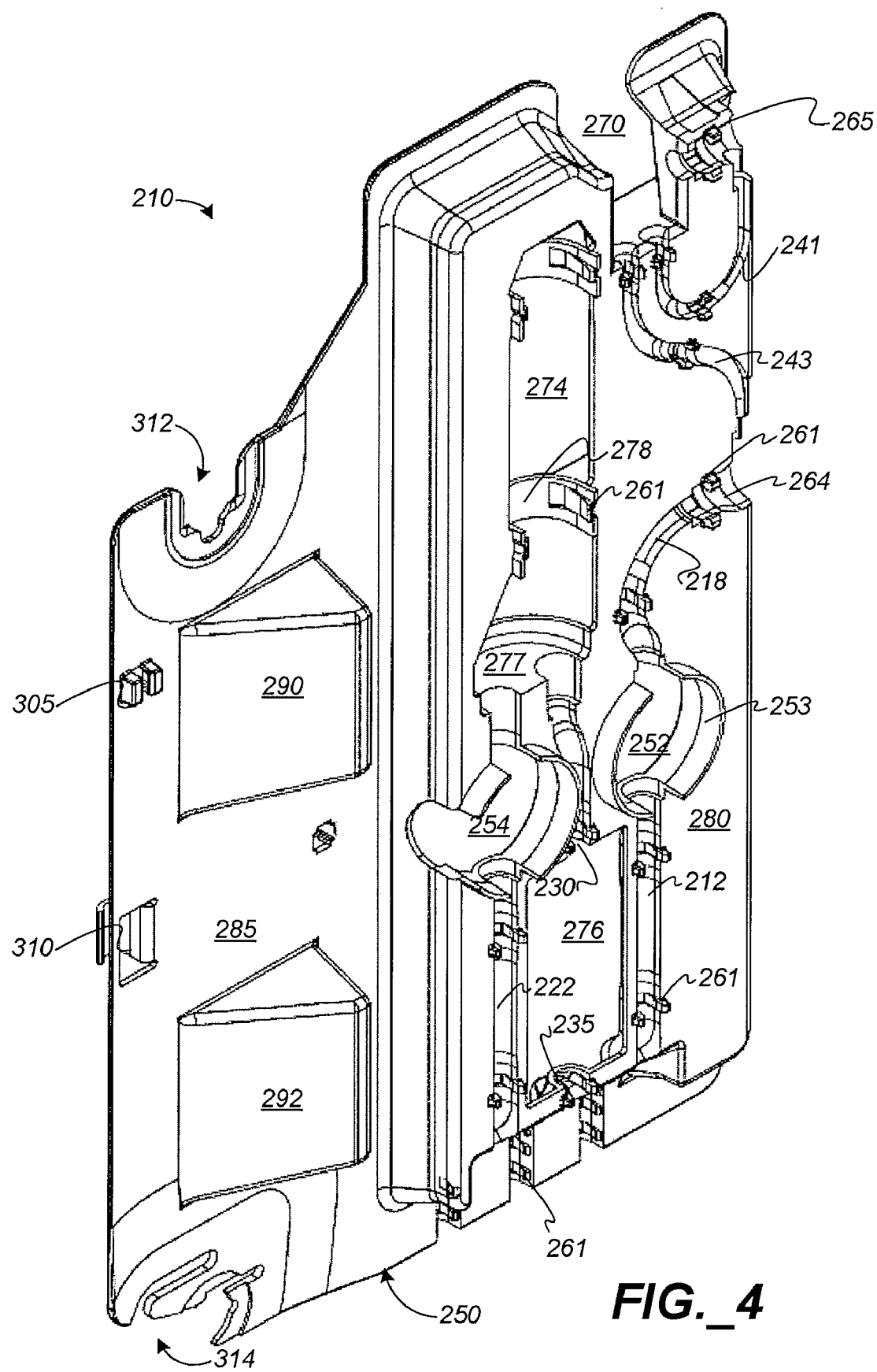
FIG._4

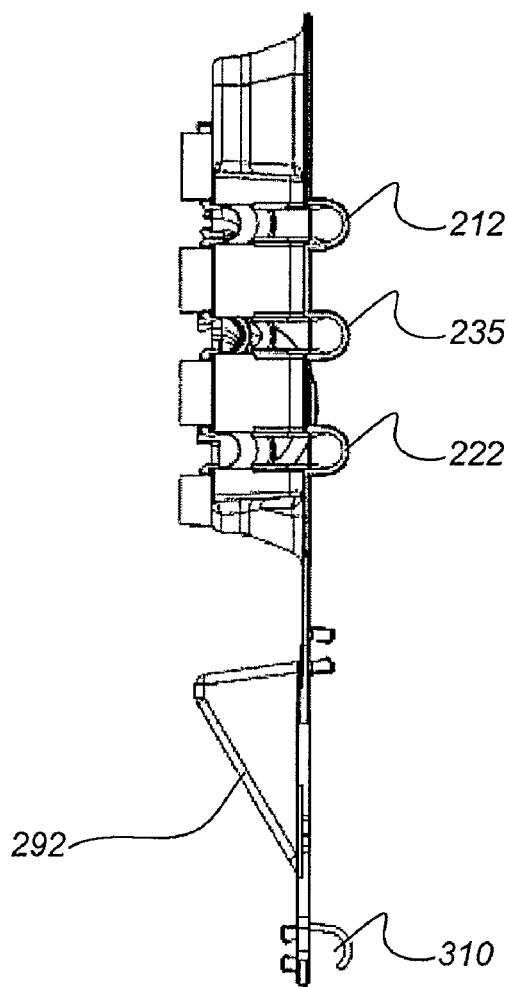
FIG._5
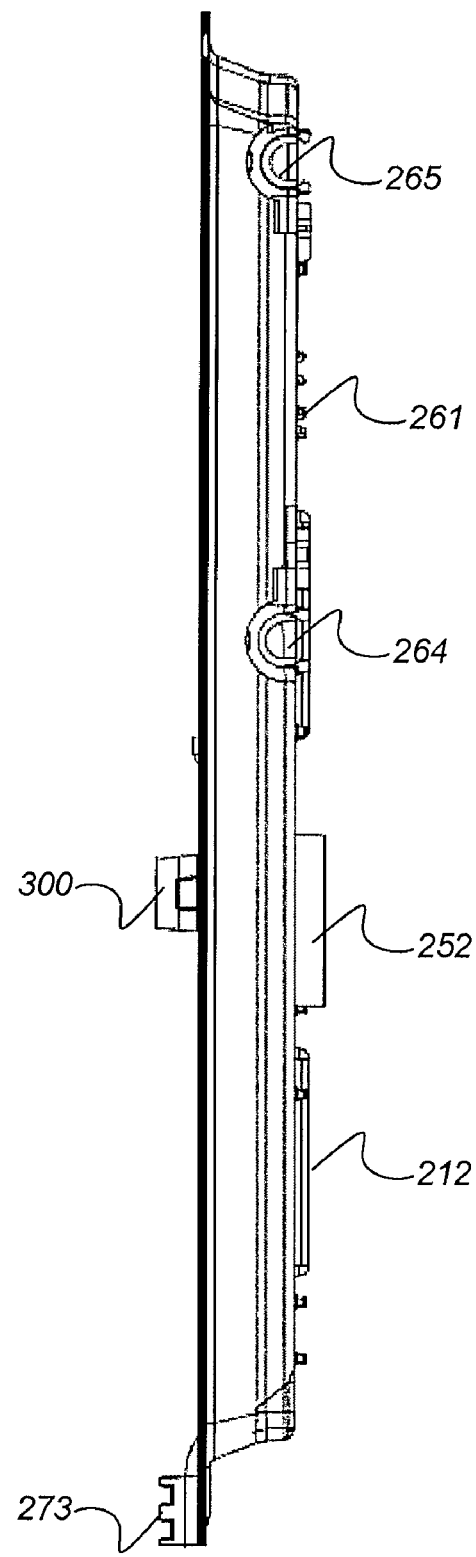
FIG._6

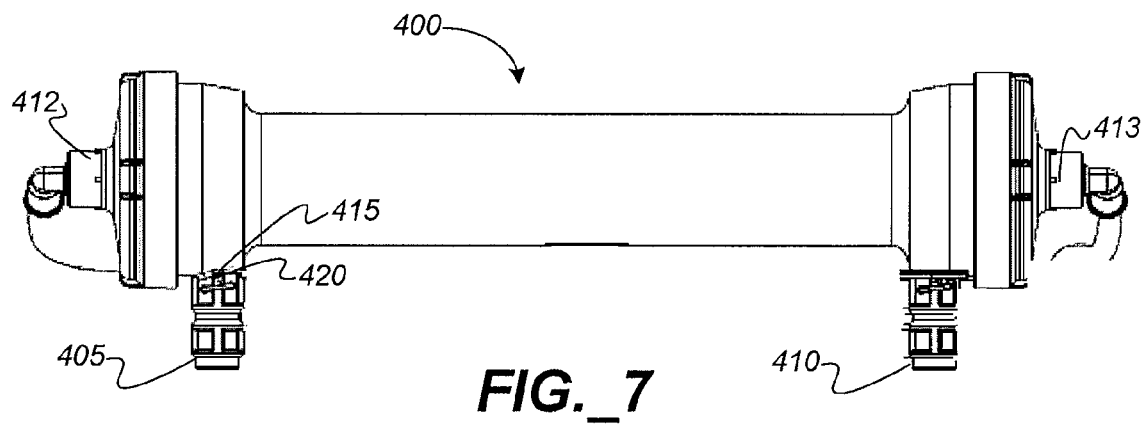
FIG._7
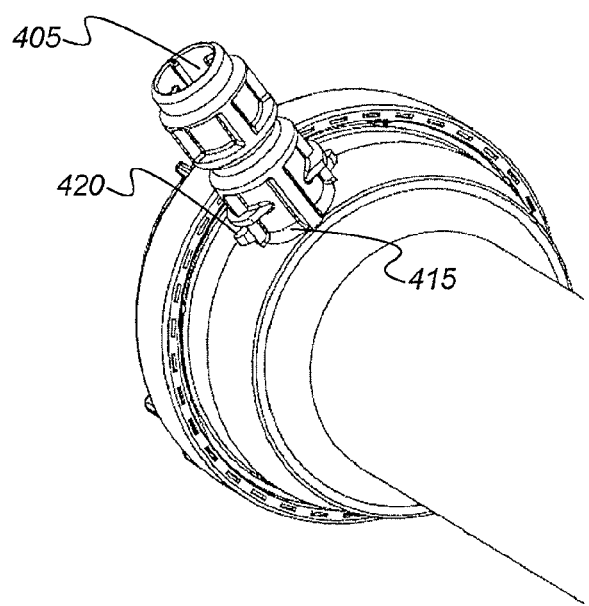
FIG._7A

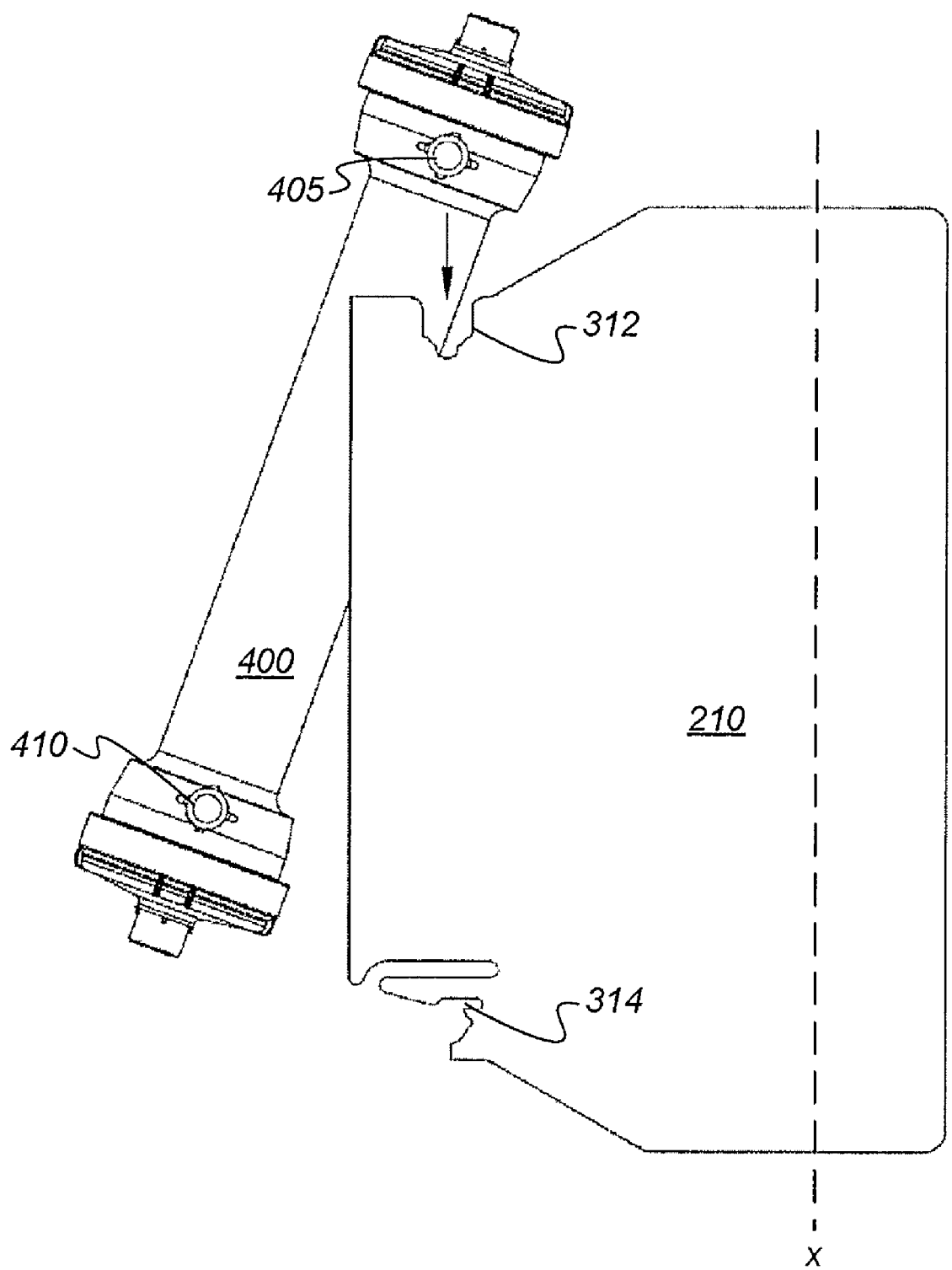
FIG._8

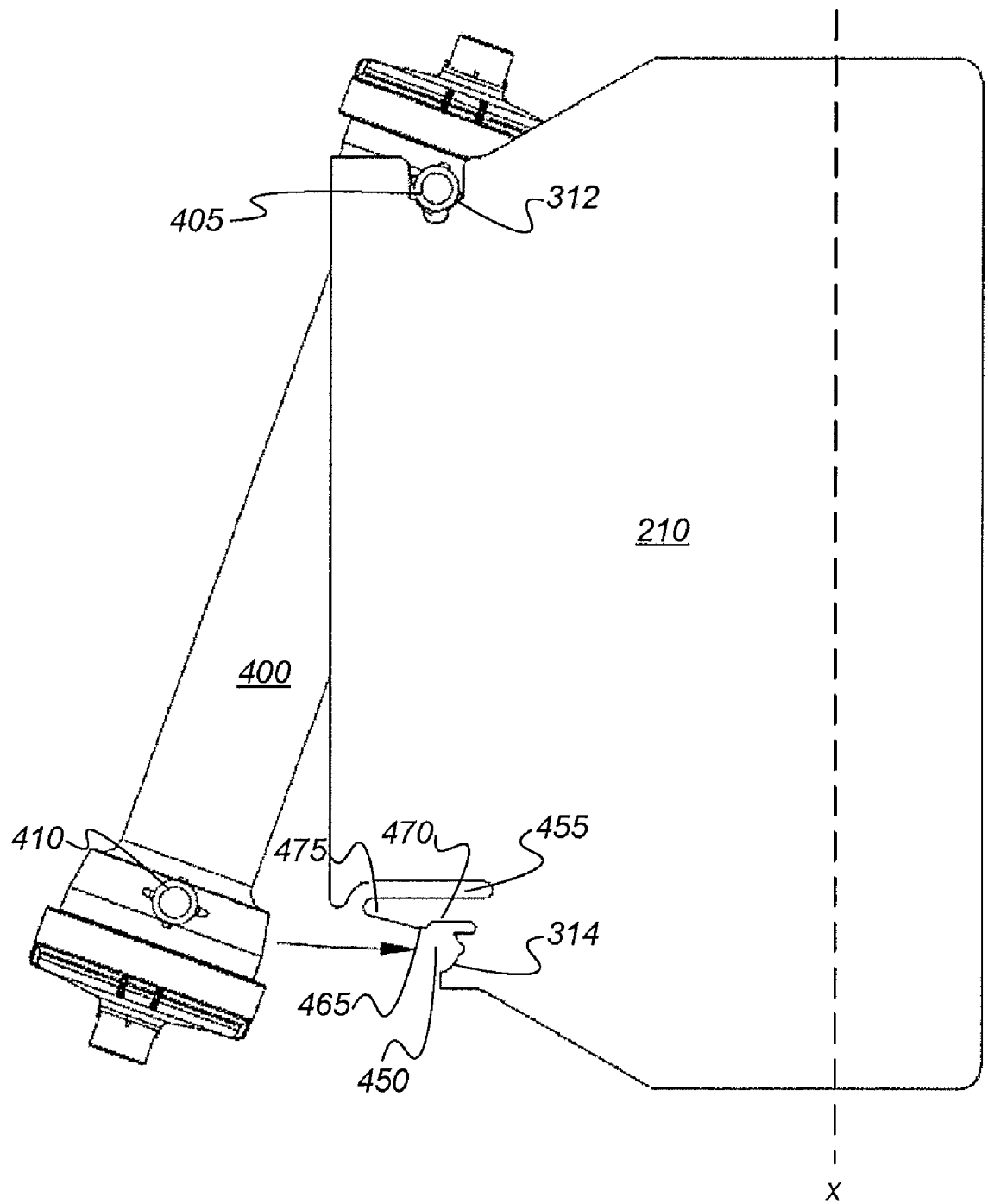
FIG._9

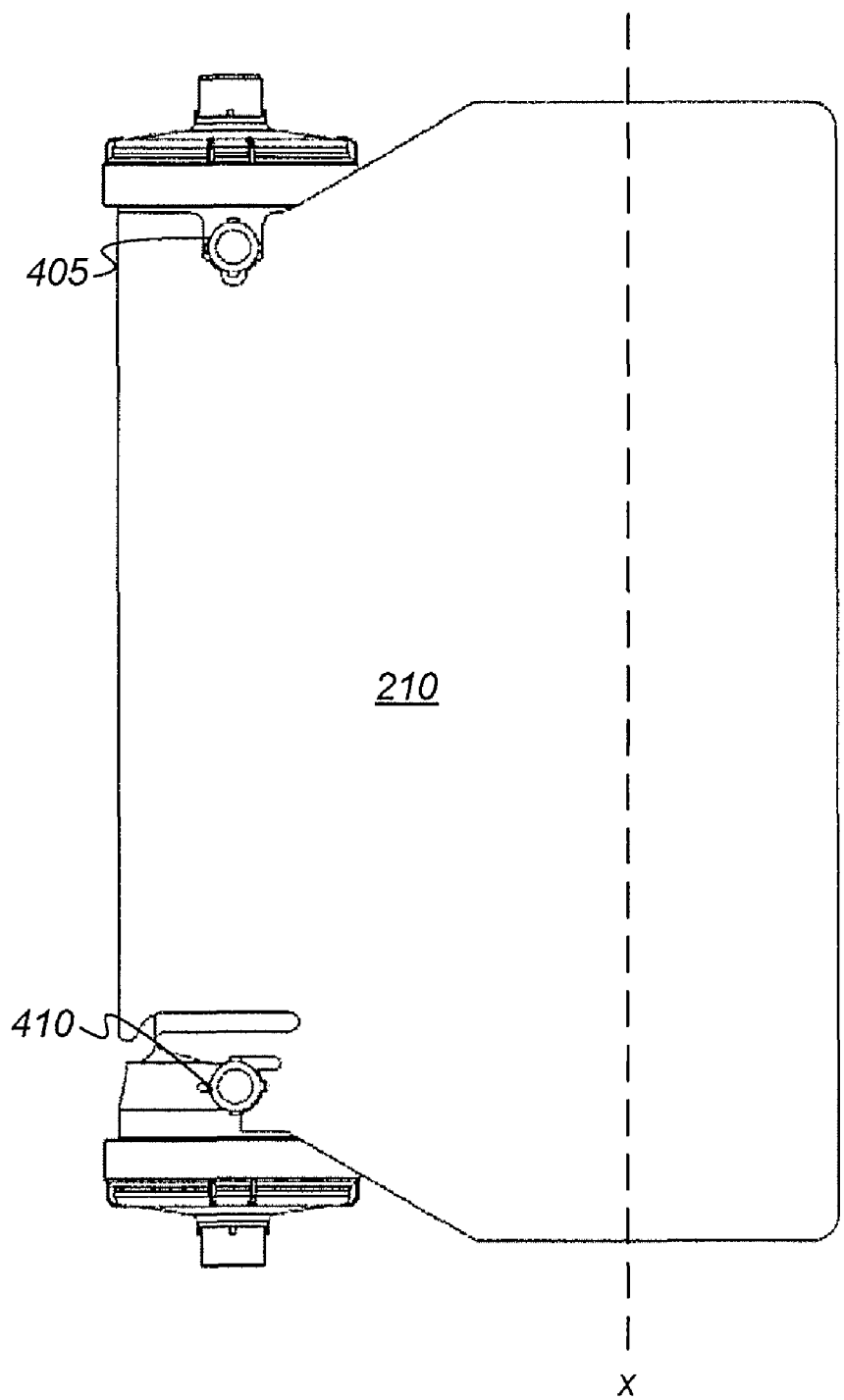
FIG._10

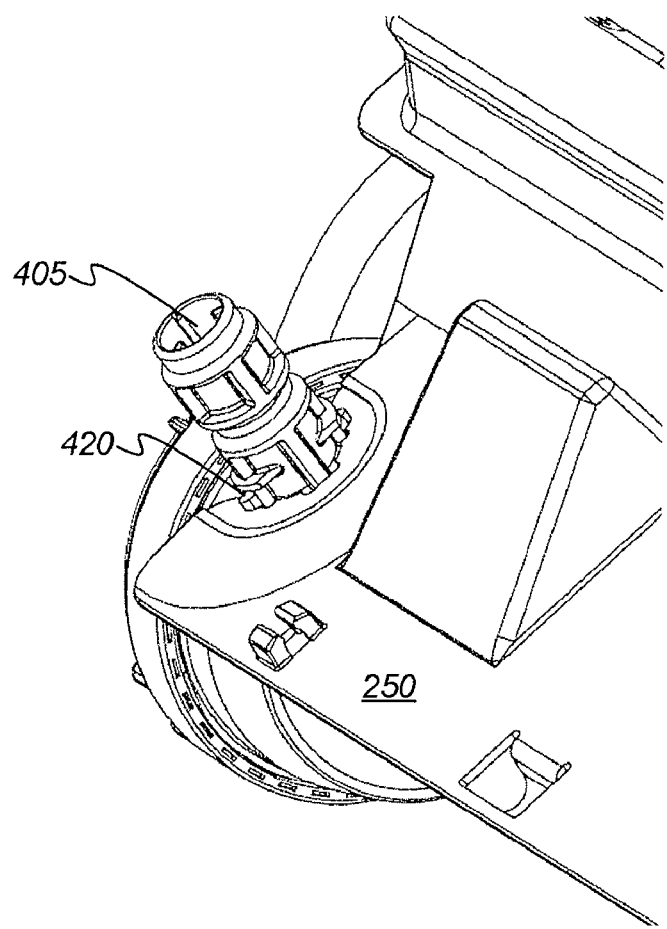
FIG._10A
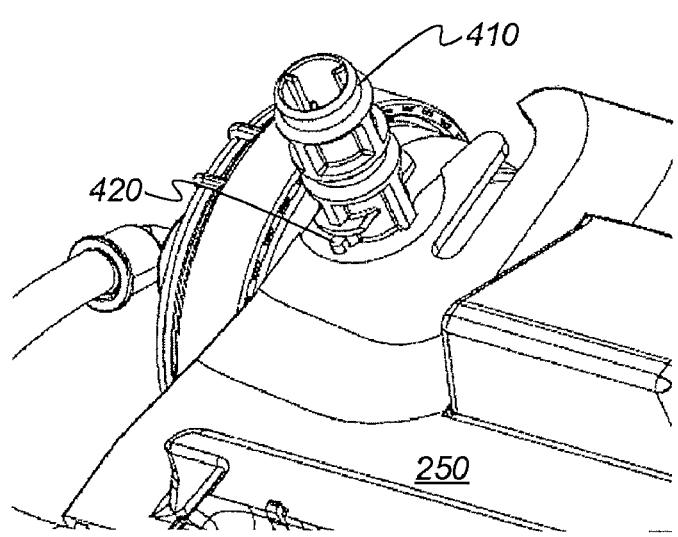
FIG._10B

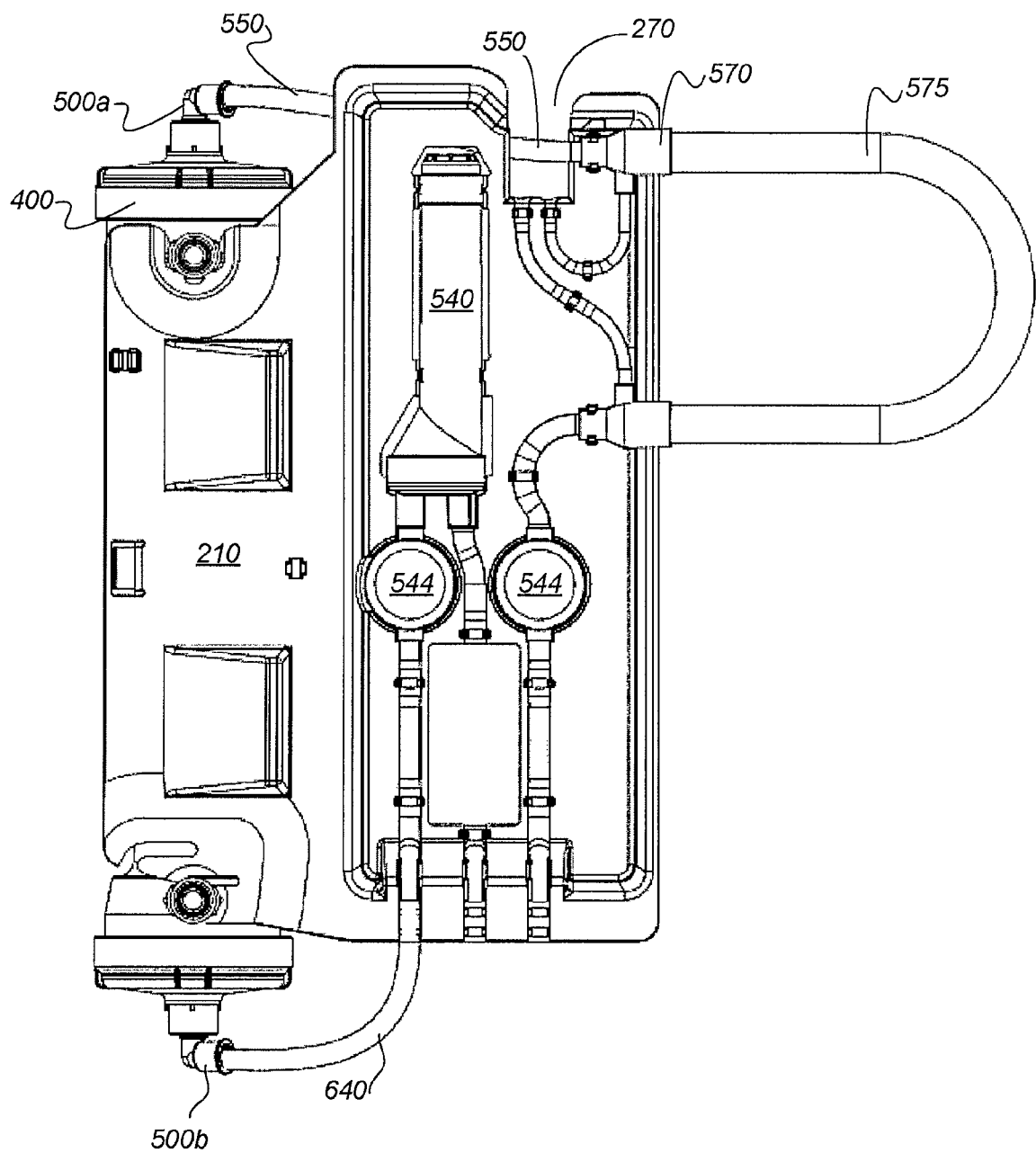
FIG._11

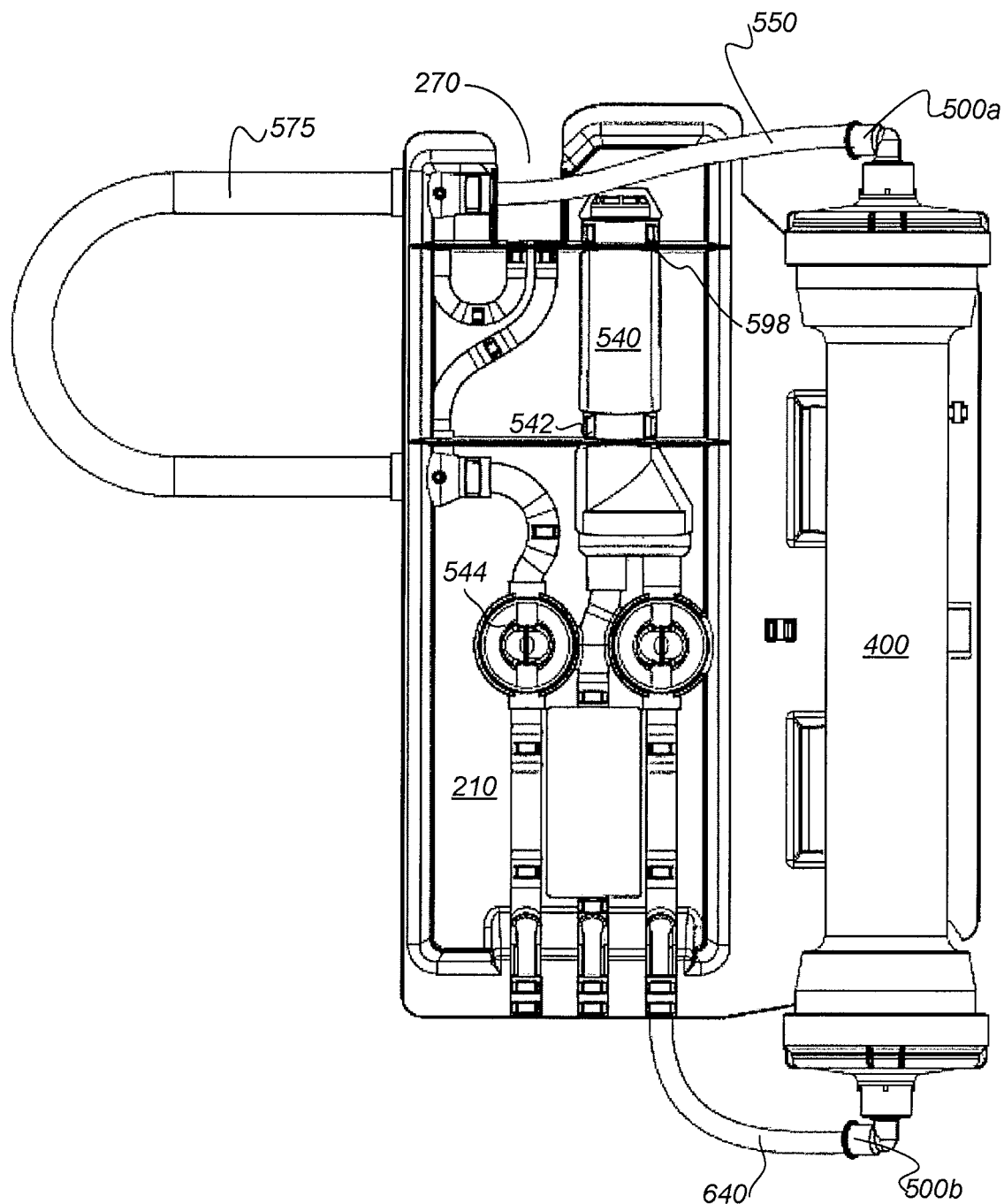
FIG._12

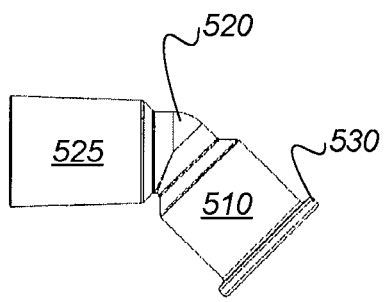
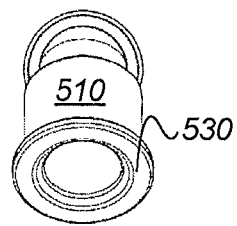
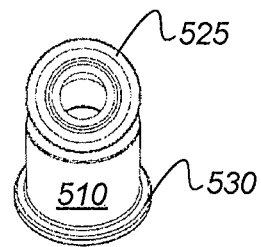
*FIG._13A*     *FIG._13B*     *FIG._13C*
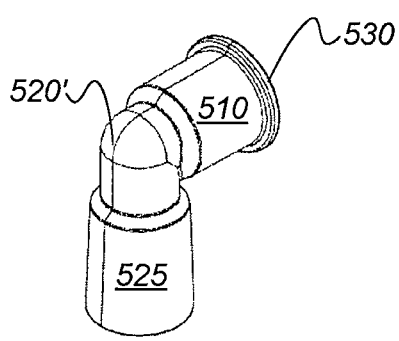
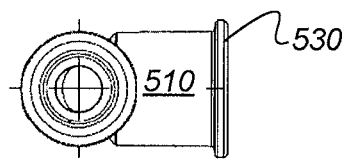
*FIG._14A*
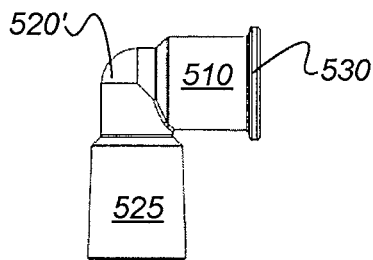
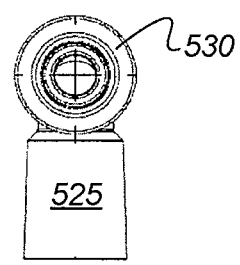
*FIG._14B*     *FIG._14C*
*FIG._14D*

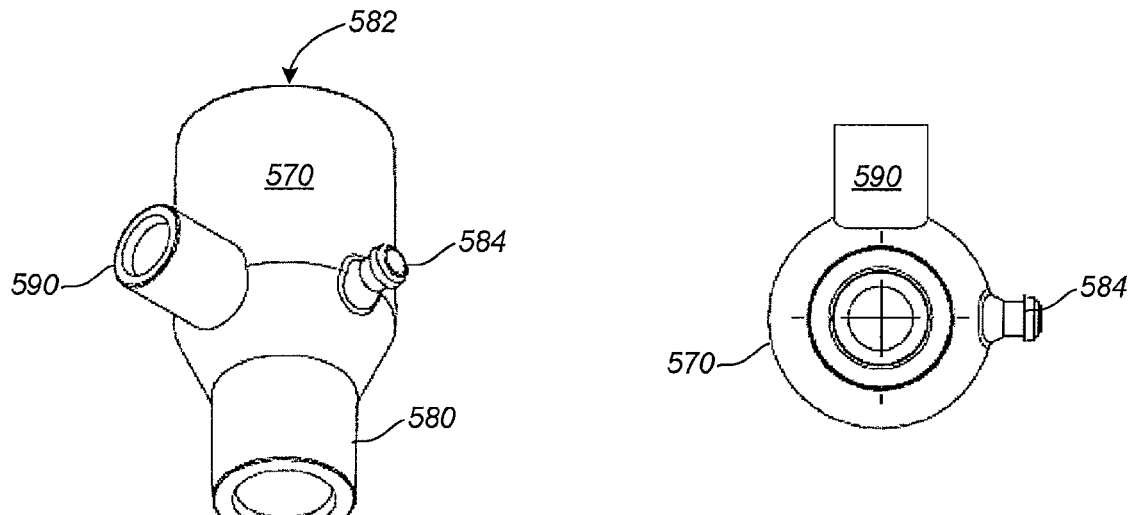
FIG._15A
FIG._15B
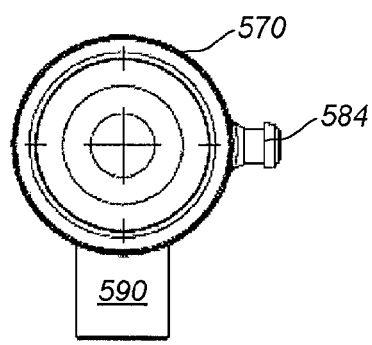
FIG._15C
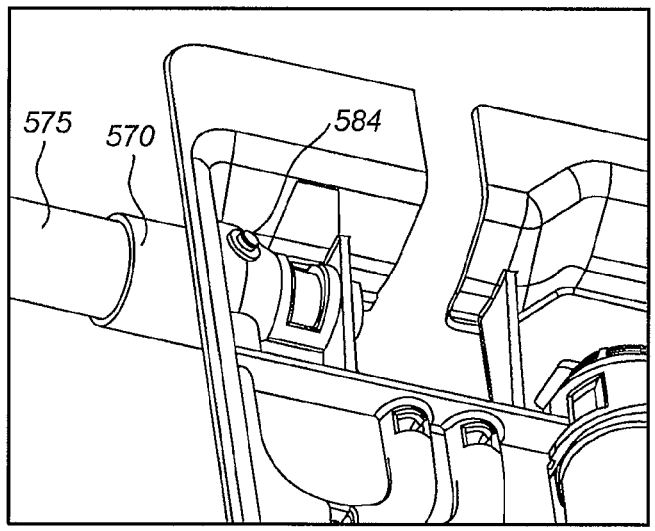
FIG._15D

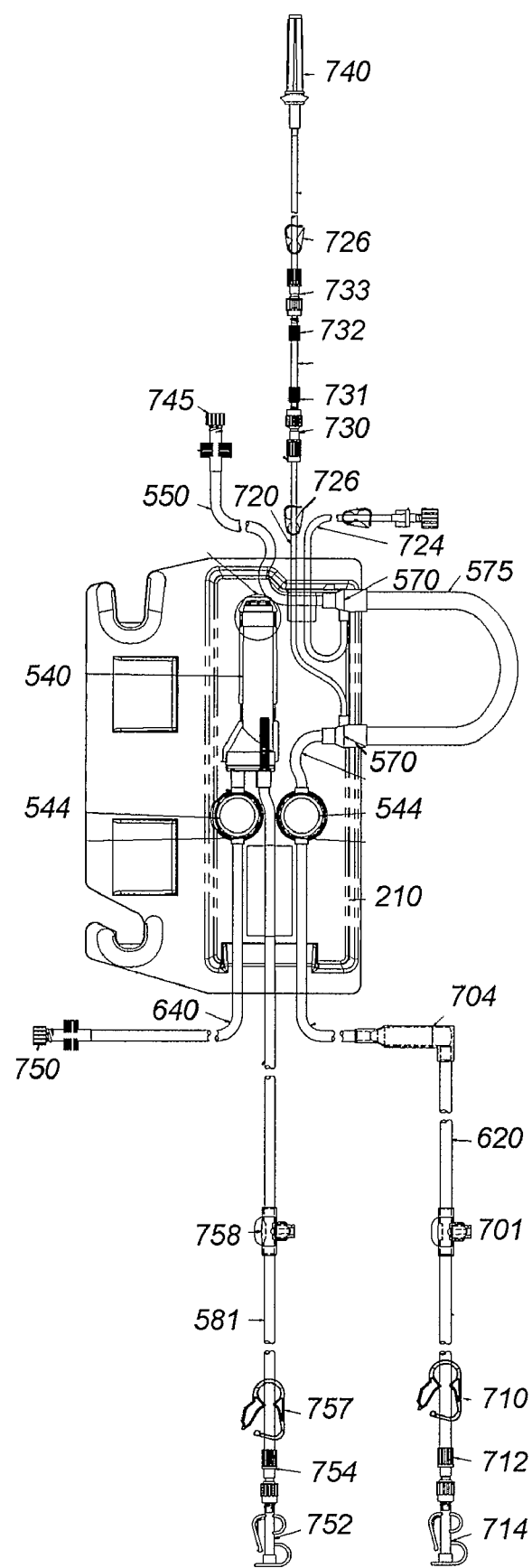
FIG._16

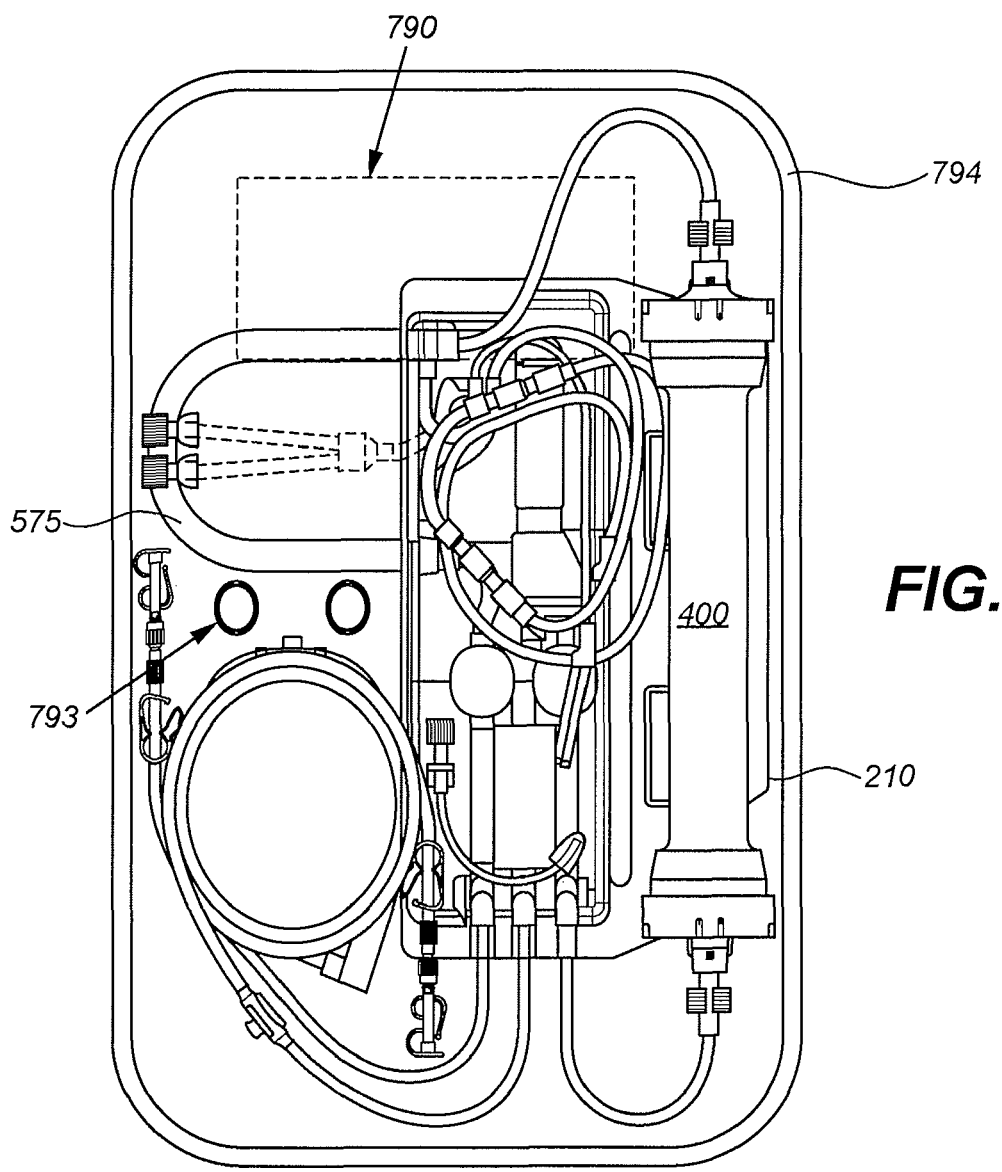
*FIG._17A*
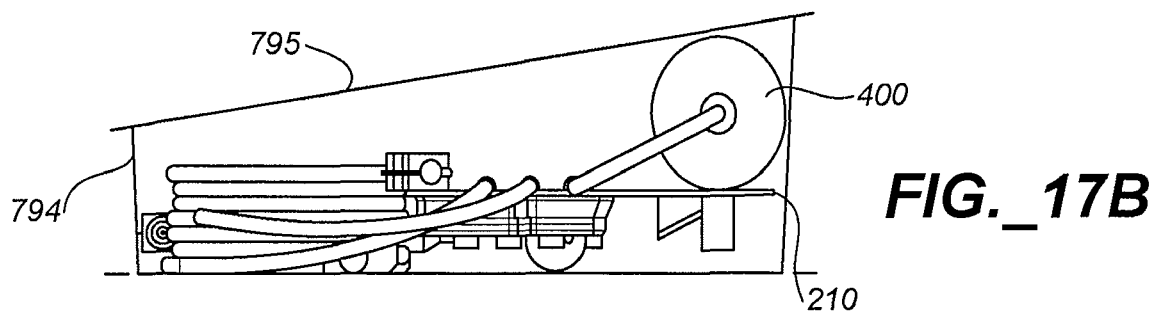
*FIG._17B*

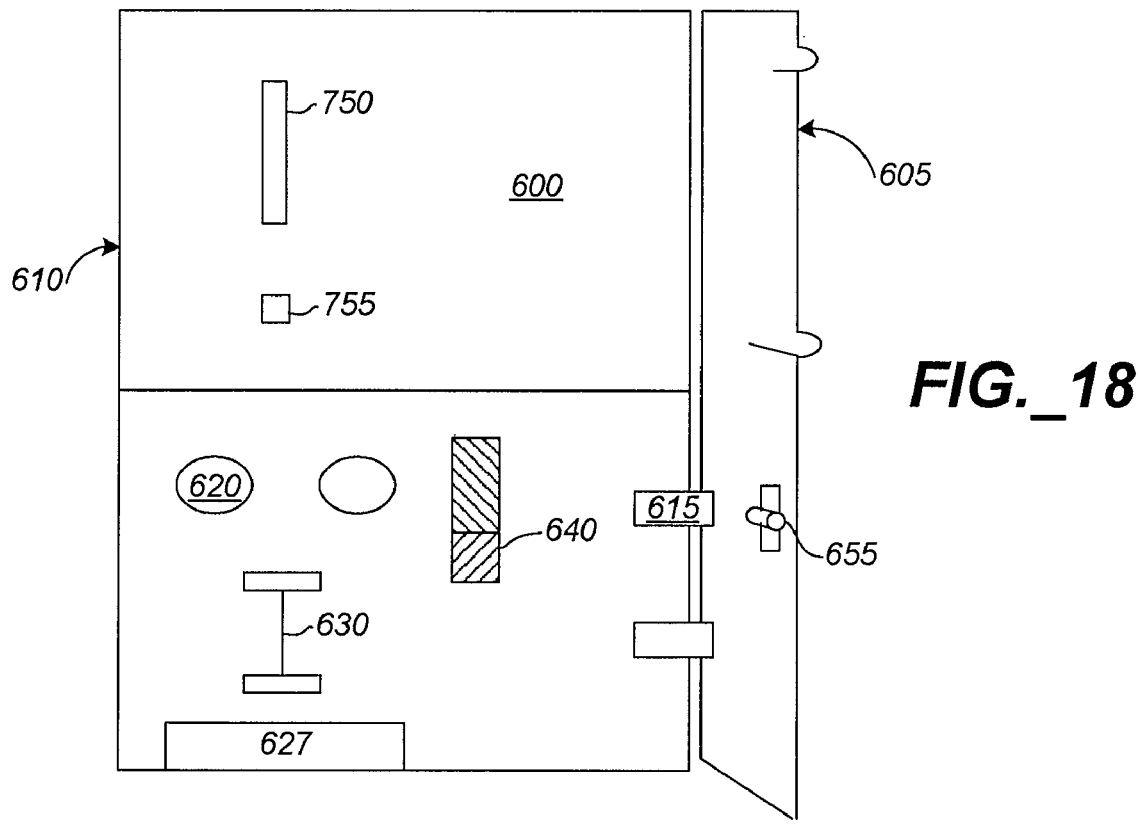
FIG._18
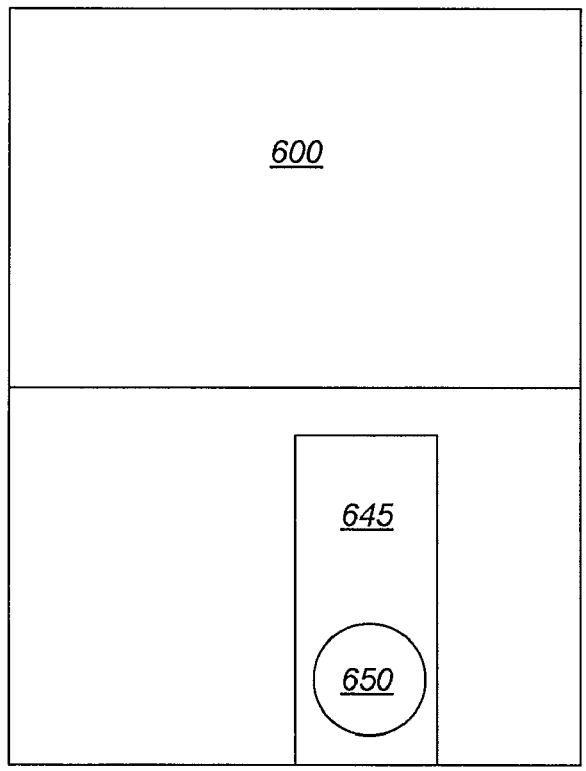
FIG._19

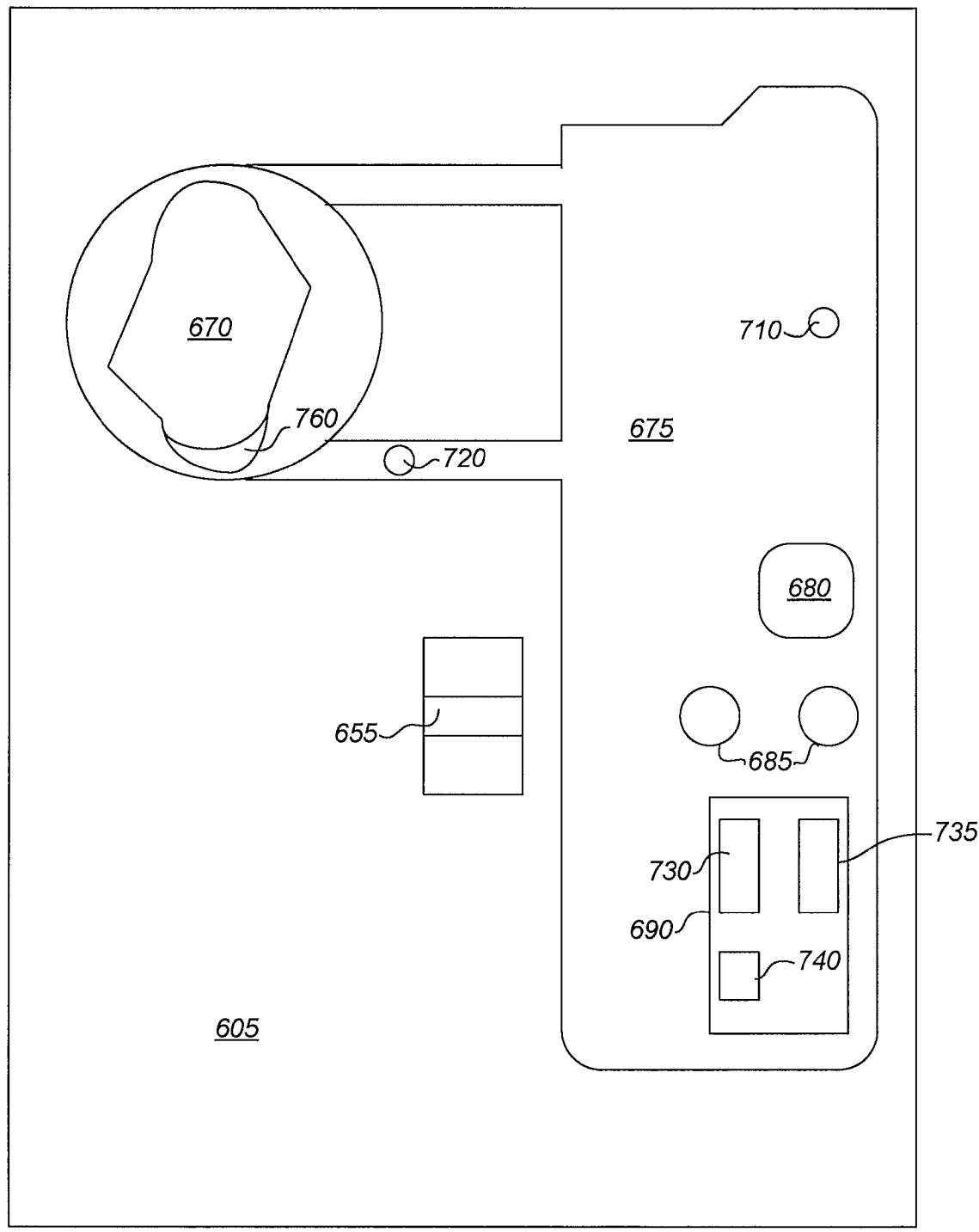
FIG._20

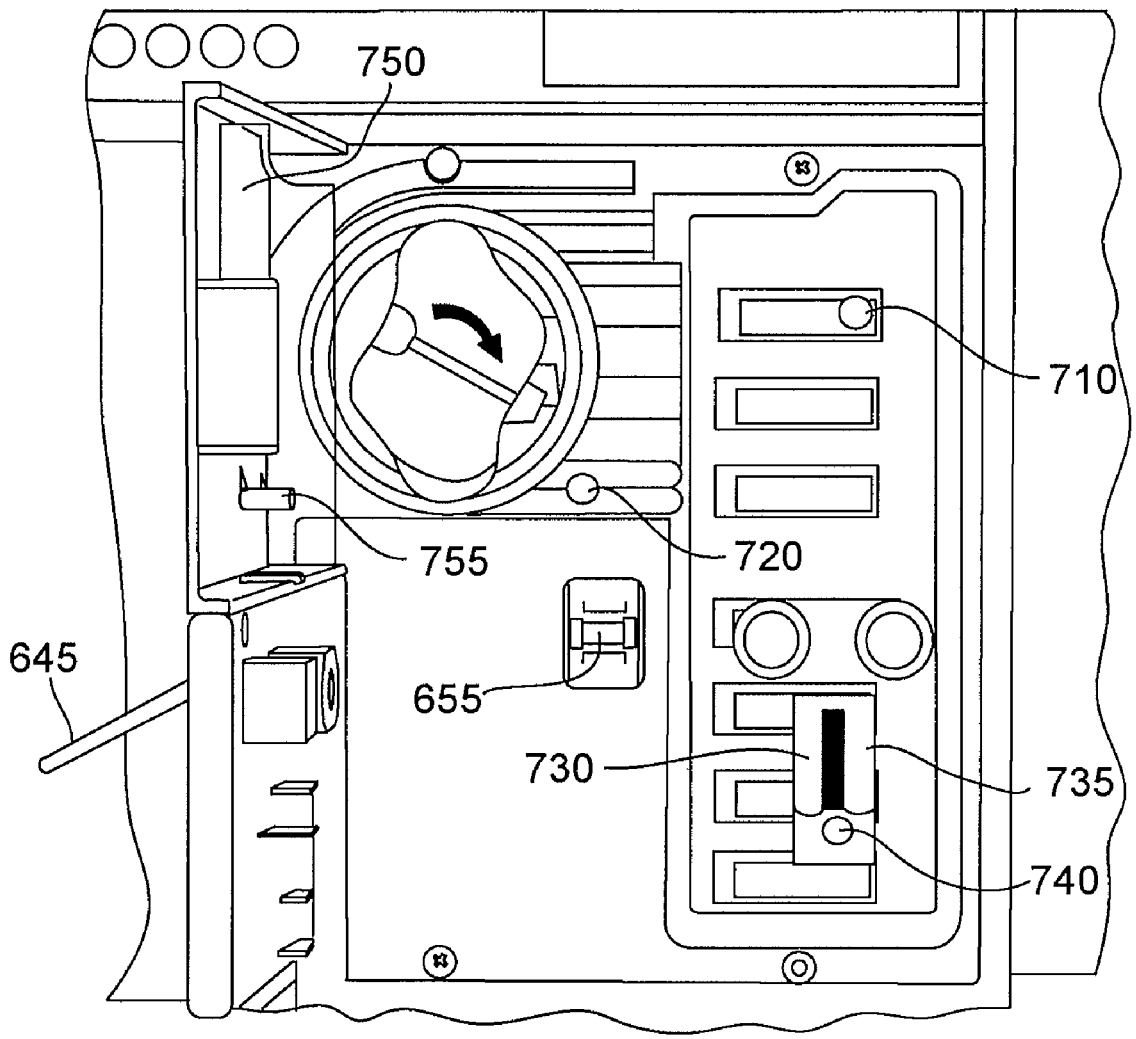
FIG._21

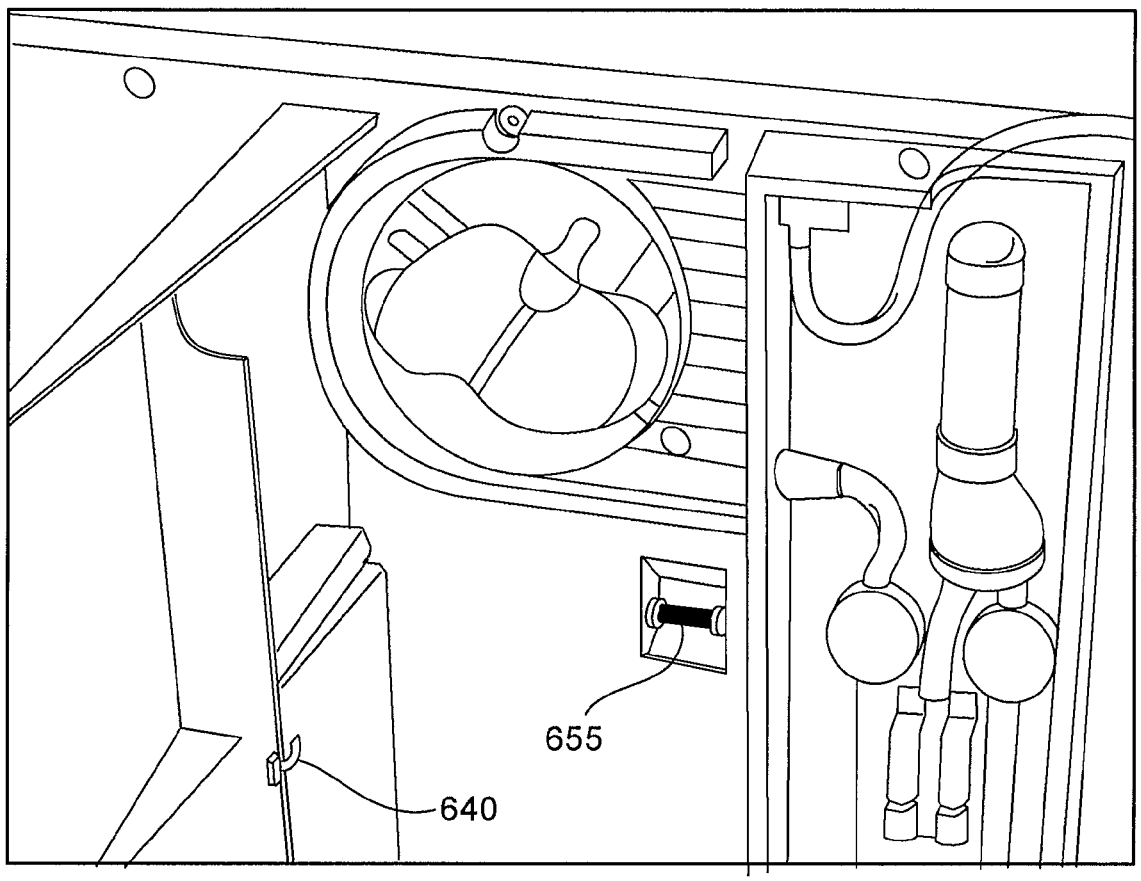
FIG._22

DIALYSIS SYSTEMS AND RELATED COMPONENTS

CROSS-REFERENCE TO RELATED APPLICATIONS

This application claims the benefit of U.S. Provisional Application Ser. No. 60/973,734, entitled "Hemodialysis Cassette" and filed on Sep. 19, 2007. The above-noted application is incorporated by reference herein.

TECHNICAL FIELD

This disclosure relates to dialysis systems and related components.

BACKGROUND

Referring to FIG. 1, a circuit 100 is shown for filtering blood from a patient 105, in a well-known medical procedure referred to as hemodialysis. In hemodialysis, blood flows through an arterial channel 120 to an arterial pressure sensor 130. The arterial pressure sensor 130 includes a transducer so that the pressure of the blood flowing through the circuit 100 on the arterial side can be monitored. The blood then flows through a portion of the channel that abuts a pump 140, such as a peristaltic pump, usually a roller type tube pump as indicated. The pump 140 forces the blood through the circuit 100. In some cases, the pressure sensor 130 is after the pump 140. The blood then flows to a dialyzer 150 and then to a venous pressure sensor 160. Next, the blood flows through the entry port of a chamber 170 in which any gas in the blood, such as air, can escape. After leaving the chamber 170, the blood travels through a venous line 180 and back to patient 105.

SUMMARY

In general, this disclosure relates to dialysis systems and related components. A cassette is described that organizes and retains a dialyzer and bloodline components, such as air release chambers and pressure chambers, and tubing, which are part of an extracorporeal blood circuit. The cassette simplifies loading and setup of a dialysis machine.

In one aspect of the invention, a hemodialysis system includes a main body, a door that can be closed relative to the main body so that an interior surface of the door is adjacent to a surface of the main body, a member that extends from the interior surface of the door, and a first sensor on the main body. The member is adjacent to the first sensor when the door is closed, and the door and the main body are arranged so that a device retaining a hemodialysis component can be disposed between the door and the main body when the door is closed.

In another aspect of the invention, a device for retaining hemodialysis circuit components includes a body having a first portion and a second portion adjacent to the first portion. The first portion has a plurality of recesses configured to retain tubes and a first aperture that intersects at least one of the recesses. The second portion has a first slot along a top edge of the second portion and a second slot along a side edge of the second portion. The first and second slots are arranged to allow the body to capture a dialyzer.

In an additional aspect of the invention, a hemodialysis circuit component kit includes a cassette including a body forming a loop adaptor recess. The portion of the body forming the loop adaptor recess has an aperture. The body has a first portion and a second portion adjacent to the first portion. The first portion has a plurality of recesses configured to retain tubes. A first aperture intersects at least one of the recesses. The second portion has a first slot along a top edge of the second portion and a second slot along a side edge of the second portion. The first and second slots are arranged to allow the body to capture a dialyzer. The kit also includes a loop adaptor in the loop adaptor recess of the body. The loop adaptor includes a locking pin disposed in the aperture in the portion of the body forming the loop adaptor recess. The kit further includes a plurality of tubes, where each tube is in a recess of the plurality of recesses, a capsule in fluid communication with a tube of the plurality of tubes, and an air release chamber in fluid communication with a tube of the plurality of tubes.

In another aspect of the invention, a device for retaining hemodialysis components includes a body forming a recessed region and an aperture that intersects the recessed region. The recessed region is configured to retain a blood line, and the aperture is configured to receive a hemodialysis component that is in fluid communication with the blood line. The body further forms a slot configured to receive and retain a fitting of a dialyzer.

Embodiments can include one or more of the following features.

In some embodiments, the member is configured to press the hemodialysis component against the first sensor when the door is closed.

In some embodiments, the hemodialysis component is a capsule with a flexible diaphragm.

In some embodiments, the hemodialysis component is an air release chamber.

In some embodiments, the hemodialysis component is tubing.

In some embodiments, the member is adapted to be displaced relative to the interior surface of the door.

In some embodiments, the member is a spring loaded member.

In some embodiments, the first sensor is a pressure transducer.

In some embodiments, the device retains tubing, a capsule with a membrane, and an air release chamber.

In some embodiments, the door is configured to retain the device against the main body when the door is closed and to apply a pressure to the capsule allowing the pressure transducer to determine a fluid pressure through the membrane.

In some embodiments, the system further includes a second sensor in the form of an optical sensor on the main body, the second sensor being positioned adjacent to an air release chamber retained by the device when the device is disposed between the door and the main body and the door is closed.

In some embodiments, the main body further includes a pump.

In some embodiments, the pump is configured so that tubing extending from the device retaining the hemodialysis component can be automatically loaded onto the pump.

In some embodiments, the main body has a recessed portion adjacent to the pump, and the recessed portion is configured to receive the device retaining the dialysis component when the device retaining the hemodialysis component is disposed between the door and the main body and the door is closed.

In some embodiments, the pump is arranged such that tubing extending from the device retaining the hemodialysis component can be operably coupled to the pump when the cassette is received within the recessed portion of the main body.

In some embodiments, the device is configured so that the device can be disposed between a door and a main body of a dialysis machine when the door is closed.

In some embodiments, the at least one of the recesses intersected by the aperture is a substantially linear recess.

In some embodiments, the first portion of the body is recessed relative to the second portion of the body.

In some embodiments, the device further includes at least one guide projecting from a back surface of the body, wherein the guide has a straight wall.

In some embodiments, the straight wall of the guide is adjacent to the first portion of the body.

In some embodiments, the recesses are semicircular recesses.

In some embodiments, the device further includes a second aperture between two linear recesses.

In some embodiments, the first aperture is circular, the second aperture is rectangular, and the cassette further includes an aperture with a tapered region. The aperture with the tapered region is closer to an upper edge of the device, the second aperture is closer to a lower edge of the device, and the first aperture is between the second aperture and the aperture with the tapered region.

In some embodiments, the device further includes a tube trap on the body.

In some embodiments, the device further includes a hook configured to position a tube on the body.

In some embodiments, the device further includes a slot extending from an edge of the device into the recessed portion.

In some embodiments, the device further includes a tubing lock adjacent to at least one of the plurality of recesses.

In some embodiments, the tubing lock includes two adjacent projections.

In some embodiments, the device further includes an aperture with crossbars, and a chamber lock adjacent to the crossbar.

In some embodiments, the aperture includes a portion with two parallel walls and a tapered portion.

In some embodiments, adjacent to the aperture is a stabilizer that extends parallel to the crossbar and to opposite sides of the recessed portion of the body.

In some embodiments, a dialyzer is held by the slot along the top edge of the second portion of the body and by the slot along the side edge of the second portion of the body.

In some embodiments, the dialyzer includes a fitting, which includes a tab that engages the body to lock the dialyzer against the body.

In some embodiments, a loop adaptor is disposed in the loop adaptor recess, and the loop adaptor includes a locking pin disposed in the aperture in the portion of the body forming the loop adaptor recess.

In some embodiments, the device includes a trap adjacent to the loop adaptor recess, and the loop adaptor is held by the trap.

In some embodiments, a plurality of tubes are in the plurality of recesses, a capsule is in fluid communication with a tube of the plurality of tubes, and an air release chamber is in fluid communication with a tube of the plurality of tubes.

In some embodiments, a dialyzer is in fluid communication with a tube of the plurality of tubes.

In some embodiments, the kit further includes a dialyzer in fluid communication with a tube of the plurality of tubes.

In some embodiments, the kit further includes a port caps, wherein the port caps are sized to fit onto end ports of the dialyzer.

In some embodiments, the kit further includes a waste bag, wherein a waste bag can be connected to a tube of the plurality of tubes.

Embodiments may have one or more of the following advantages. Many or all of the disposable components used when filtering a patient's blood with a dialysis machine are captured by a single device (e.g., a single cassette). The device obviates the need for a user, such as a nurse or health aid, to have to load each of the components into the dialysis machine separately. All of the components can be packaged as a set, helping to ensure that no components are forgotten prior to connecting a patient to the dialysis machine. Further, because all of the components can be provided to the user without the user having to prepare each individual component, there is little risk that used components will accidentally be used a second time. This reduces the risk of patient contamination. The device is configured to be quickly and easily loaded into the dialysis machine, so that risk of user error or incorrect alignment with the dialysis machine is reduced. Specifically, the device can include guides that assist the user in properly lining the device up with the dialysis machine. The device can include additional traps for capturing tubing and easily releasing the tubing when the tubing is required by the user. Because all of the components can be received by a user as an integral kit, time for setting up a dialysis machine for performing dialysis is reduced and the simplicity is increased. The device can lead to safer and speedier patient care.

Other aspects, features, and advantages of the invention will be apparent from the description and drawings, and from the claims.

DESCRIPTION OF DRAWINGS

FIG. 1 is a schematic depiction of a hemodialysis system.
FIG. 2 is a front view of a cassette.
FIG. 3 is a perspective view of a cassette.
FIG. 4 is a back view of a cassette.
FIG. 5 is a bottom view of a cassette.
FIG. 6 is a side view of a cassette.
FIG. 7 is a side view of a dialyzer.
FIG. 7A is a perspective view of one end of a dialyzer.
FIGS. 8-10 are undetailed back views of the cassette of FIG. 2 with the dialyzer of FIG. 7, showing the steps of inserting the dialyzer into the cassette.
FIGS. 10A and 10B are backside detail perspective views of the top and bottom fittings on the dialyzer holding the dialyzer in the cassette.
FIG. 11 is a back view of the cassette of FIG. 2 with components inserted into the cassette.
FIG. 12 is a front view of the cassette of FIG. 2 with components inserted into the cassette.
FIGS. 13A-C are side, top and front views of a 45° tube adaptor for the dialyzer ends.
FIGS. 14A-D are profile, side, bottom and front views of a 90° tube adaptor.
FIGS. 15A-C are perspective, bottom and top views of a pump loop adaptor.
FIG. 15D is a close up view of a loop adaptor in a cassette.
FIG. 16 is a back side view of a cassette holding tubing.
FIG. 17A is a top view of a cassette holding tubing and components in packaging.
FIG. 17B is an end view of a cassette holding tubing and components in packaging.
FIG. 18 is a schematic of an inside of a door on a hemodialysis machine.

FIG. 19 is a schematic of an outside of a door on a hemodialysis machine.

FIG. 20 is a schematic of a recessed compartment of a hemodialysis machine which the door in FIGS. 18 and 19 covers when closed.

FIG. 21 is a picture of a part of a hemodialysis machine with the door open.

FIG. 22 is a picture of a part of a hemodialysis machine with a cassette in the machine.

DETAILED DESCRIPTION

Referring to FIGS. 2-6, a dialysis cassette 210 is configured for holding components used to direct extracorporeal fluid through a hemodialysis process, such as an air release chamber, tubing and a dialyzer (not shown in present figures). The cassette 210 has a transparent, (molded thermoplastic or thermoset) cassette body 250, which includes apertures and recesses for capturing the components and for allowing for visual or instrumentational access to the components. The body 250 includes a recessed portion 280, shown on the left side of FIG. 2, and a flat portion 285, shown on the right side of FIG. 2. The recessed portion 280 is configured to retain most of the components while the flat portion 285 is configured to hold the dialyzer. One, two or more optional stabilizers 269 (shown in FIG. 3) provide stability to the recessed portion of the cassette 210.

Recesses 212, 218, 222, 230, 235, 241 and 243 with a semicircular profile are configured to retain tubing. In some embodiments, the recesses 212, 218, 222, 230, 235, 241 and 243 extend out of the front of the body 250 and the tubes are positioned on a back side of the body 250 when placed into the cassette. Thus, from a back side of the cassette 210, as shown in FIG. 4, the recesses 212, 218, 222, 230, 235, 241 and 243 appear concave, that is, as recesses. From a front side of the cassette, as shown in FIG. 2, the recesses 212, 218, 222, 230, 235, 241 and 243 appear convex or as embossed features. In some embodiments, the recesses 212, 218, 222, 230, 235, 241 and 243 do not extend beyond the plane of the flat area 285.

In some embodiments, the portions of the cassette body 250 that form the recesses have apertures 260 formed therein (e.g., FIG. 2), which allow a user to see whether the tubing is properly seated in a recess and allow the tubing the freedom to bend within a range of angles. Thus, the apertures 260 can facilitate placing and retaining the tubing within the recesses of the cassette body 250. Apertures 260 can also facilitate forming projections 261 (shown in FIG. 4), such as during a molding process, that capture and retain the tubing and components. Two projections 261 can be on opposite sides of a recess from one another. The portion of the projection 261 that extends furthest from the body can be closer to the opposite projection 261 than any other portion of the projection. Thus, the projections 261 can extend around the tubing or components and hold tubing or components in the recess or aperture. In some embodiments, the projections 261 are wider at a location further from the body 250 than at a location closer to the body 250.

In some embodiments, at a bottom end of the recessed portion 280 the cassette transitions to the flat portion 280. At this transition, recesses 212, 235 and 222 have end pieces 273 that project frontward from the flat portion 285, as shown in FIG. 6.

In some embodiments, the cassette body 250 has apertures 252, 254 that are wider than a width of the recesses and that intersect one or more of the recesses. The apertures 252, 254 allow for access to components located along the tubing, which are discussed further below. In some embodiments, a boss 253 (shown in FIG. 4) surrounds apertures 252, 254 and extends from the rear of the cassette. In some embodiments, apertures 252, 254 are adjacent to one another. In some embodiments, the cassette 210 includes deeper recessed regions 264, 265 for capturing tubing adapters, also discussed further below. In addition, an optional slot 270 in an upper edge of the body 250 allows for the tubing to be fed from one side of the body 250 to the other, such as from the front to the back.

Aperture 274 allows space for an air release chamber to be captured by the cassette 210. Suitable air release chambers are described in U.S. Publication No. 2007/0106198, published May 10, 2007, and also in U.S. Patent Application Ser. No. 60/973,730, entitled "Safety Vent Structure for Extracorporeal Circuit" and filed on Sep. 19, 2007, each of which is incorporated herein by reference. Aperture 274 can be divided into two, three or more parts by cross bars 278 that, in some embodiments, are configured to allow the air release chamber to be snapped or press fit into the cassette body 250. A floor 277 that partially defines aperture 274 provides a seat for the air release chamber when inserted into the cassette 210. In some embodiments, the aperture 274 has a middle portion with parallel walls and a lower portion, which is adjacent to the floor 277 with one wall that is parallel to a wall in the center portion and one wall that is at an angle to the wall in the center portion. Thus, in a lower region of the aperture, i.e., adjacent to floor 277, the aperture 274 tapers to a rectangular region. Optional aperture 276 enables a sensor to access any tubes exposed by the aperture 276.

The layout of one particular cassette 210 is described below. Within the recessed portion 280, the recesses 212, 235 and 222 are parallel to one another and extend towards a bottom of the cassette. Aperture 276 is between recesses 212 and 222. Above and to the left and right of aperture 276 are apertures 252 and 254. Between apertures 252, 254 is recess 230. Recess 230 is an extension of recess 235, with aperture 276 therebetween. Above aperture 252, which extends from recess 212, is recess 218, which curves towards the left of the cassette and opens to the side of the cassette through deeper recessed region 264. A first support 269a is above recess 218. Between first support 269a and second support 269b are recesses 241 and 243. Recess 243 leads from deeper recessed region 264, which is just below support 269a, up through second support 269b and into slot 270 in the top of the cassette. Recess 241 leads from slot 270 through second support 269b and forms a unshaped curve to connect to deeper recessed region 265 in the upper left corner of the cassette 210. The deeper recessed region 265 is between the second support 269b and the top of the cassette 210. Above aperture 254, which intersects recess 222, and recess 230 is floor 277 and aperture 274.

In some embodiments, the flat portion 285 (shown in FIG. 3) of the cassette body 250 includes one, two or more guides or supports 290, 292 for positioning and supporting the cassette against a dialysis machine. A guide has a straight wall that projects at an angle of about 75° to about 90° (e.g., about a 90° angle or about a 75° angle) from the back of the cassette and that is parallel to a main vertical axis or x axis of the cassette (shown in FIG. 2). The wall of the guide is closer to the recessed region 280 than the rest of the guide.

In embodiments, the flat portion 285 includes traps 300, 305 and/or hook-shaped extensions 310 for capturing the tubing. The traps 300 can extend outwardly from a front of the cassette body 250, or the traps 305 can extend outwardly from the back of the cassette body 250. In embodiments, the traps include two parallel L-shaped projections where a short part of the "L" of each projection extends towards the other projection. The opening between the two projections is smaller than a diameter of the component that the trap is configured to retain. The flexible nature of either the component being trapped or the trap itself allows one of the items to bend so that the component can be secured in the trap or released from the trap with a small amount of force. The flat area can also include slots 312, 314 for capturing and retaining fittings from the dialyzer, which is discussed further below.

The cassette 210 is configured to hold and retain a dialyzer 400 of the type illustrated in FIGS. 7 and 7A, for example. The dialyzer 400 has fittings 405, 410 on either end that extend in the same direction from the dialyzer 400, such as at a 90° angle to a main axis of the dialyzer body. In some embodiments, the fittings 405, 410 provide an entry and exit for dialysate into and out of the dialyzer. Each fitting 405, 410 has two tabs 420 adjacent to a base 415 of the fittings 405, 410. The base 415 of the fitting can be trapped by the slots 312, 314 in the cassette 210 and the dialyzer 400 is held close to the body 250 by tabs 420. The tabs 420 hold the dialyzer 400, preventing the dialyzer 400 from being held loosely by the cassette 210. In some embodiments, the base 415 of the fitting 405, 410 between the dialyzer body 400 and the tab 420 has a width that is only slightly greater than a thickness of body 250 around the slots 312, 314.

Referring to FIG. 8, the dialyzer 400 is positioned for capture by the cassette 210. One extension or fitting 405 of the dialyzer 400 is positioned above an upper slot 312 in the cassette 312. The dialyzer 400 can be at an angle to a vertical axis x of the cassette 210 so that the lower fitting 410 does not interfere with the cassette body. The upper slot 312 is in the upper surface of the cassette 210. In some embodiments, the upper slot 312 can taper down as the slot 312 extends into the cassette 210, that is in a "V" shape. In some embodiments, the slot has a "U" shape, that is the slot has sidewalls that are parallel to one another and a flat or curved bottom. In some embodiments, a portion of the slot is just slightly greater than the fitting 405, 410 on the dialyzer 400, specifically just slightly greater than the outer diameter at the portion with a small outer diameter 415 (shown in FIG. 7).

Referring to FIG. 9, the dialyzer 400 is then rotated about the axis of the fitting 405 in the slot 312 so that the longitudinal axis of the dialyzer 400 is positioned parallel with the vertical axis x of the cassette 210. This action brings a lower extension or fitting 410 into the lower slot 314 of the cassette 210. The lower slot 314 is in a side surface of the cassette 210. In some embodiments, the lower slot 314 has a primary slot 450 in which the lower fitting 410 fits into and a secondary slot 455. Between the primary slot 450 and the secondary slot 455 is a resilient tongue or tab 475. The tab 475 is narrower at a portion 470 adjacent to the portion of the primary slot 450 that captures the fitting 410 than at a location 465 on the tab 475 just beyond where the fitting 410 is captured and retained. The wider portion of the tab at location 465 serves to hold the fitting 410 locked in place and can inhibit (e.g., prevent) the dialyzer 400 from being inadvertently released from the cassette 210. As the dialyzer 400 is rotated into place, the fitting 410 presses on the tab 475, causing the tab 475 to bend towards the secondary slot 455 to make room for the fitting 410 to fit into the primary slot 450. Once the fitting 410 is fully seated in the primary slot 450, the tab 475 moves back into its un-bent position and holds the fitting in place. In some embodiments, the tab 475 tapers down from the location 465 where the tab 475 is wide to the tip of the tab 475 to facilitate guiding the fitting 410 into place.

As shown in FIG. 10, the dialyzer 400 is press fit or snapped into place so that the dialyzer 400 is securely locked into place and the cassette 210 will generally not release the dialyzer 400 without the dialyzer 400 being forced from the cassette 210. FIGS. 10A and 10B show close up views of the tabs 420 on the top fitting 405 and bottom fitting 410, respectively, holding the dialyzer 400 close to the cassette 210.

Referring to FIGS. 11 and 12, the dialyzer 400 is secured to the cassette 210 and is connected to tubing held by the cassette 210. A tube adaptor 500a is connected to one end of the dialyzer 400. The other end of the tube adaptor 500a is connected to tubing 550. Similarly, a second tube adaptor 500b is on the other end of the dialyzer and connected to tubing 640.

Referring to FIGS. 13A-14D, each of the tube adaptors 500a and 500b have a straight portion 510 which fits over a luer taper on a dialyzer end cap. An elbow portion 520 connects the straight portion to a tube connector 525. The elbow portion 520 can be at a 45° angle or the elbow portion 520' can be at a 90° angle. Other angles for the elbow are also possible, such as 60°. The tube adaptor not only provides a connection between the dialyzer and the tubing, but also provides a bend in the fluid line. In some embodiments, the tube adaptor is formed of a rigid material, unlike the tubing. In some embodiments, the tube adaptor is semi-rigid or soft, but has a harder durometer value than the tubing. If the tubing were forced to bend, such as at a 45° or 90° angle, the tubing could bend over on itself and crease shut, preventing the flow of fluid through that portion of the tubing. Conversely, the tube adaptor has a built-in elbow that allows a bend in the circuit without a part of the circuit clamping closed and preventing fluid flow.

The straight portion 510 includes an external ring or flange 530. The flange 530 increases the outer diameter of the straight portion 510 at the end of the straight portion. The flange 530 helps to prevent the tube adaptor from being connected to the dialyzer or tubing the wrong way. This prevents the incorrect engagement of an end of the straight portion 510 with the dialyzer end cap by providing interference with the internal diameter of the threads on the dialyzer end cap.

Referring back to FIGS. 11 and 12, in some embodiments the tubing 550 extends from the tube adaptor 500a across the front of the cassette 210 through slot 270 to the back of the cassette 210. The tubing 550 then connects to a pump loop adaptor 570, which is held by a recess 265 in the cassette 210. The pump loop adaptor 570 is connected to a pump loop 575, which fits around a pump, as described further below. The pump loop 575 can be similar to the tubing 550. In some embodiments, the pump loop 575 is formed from a wider diameter tubing than the tubing 550.

Referring to FIGS. 15A-C, the pump loop adaptor 570 includes a connector portion 580 configured to connect to the tubing 550. On an opposite end, the pump loop adaptor 570 includes an end 582 configured to connect to the pump loop 575. Between the end 582 and the connector portion 580, the adaptor 570 has a tapered portion. Optionally, the pump loop adaptor 570 also includes a locking pin 584 that snaps into the cassette 210 through a hole to provide secure retention of the adapter in the cassette 210, as shown in FIG. 15D. Pin 584 has a slightly enlarged annular boss formed on the end with a tapered leading edge, as shown in FIG. 15B, so that when press fit through the corresponding hole in the cassette, the pin snaps securely in place with the annular boss protruding from the other side of the cassette as shown in FIG. 15D. Optionally, the pump loop adaptor also includes a side entry extension 590, which can be used for introducing other fluids into the circuit.

Referring back to FIGS. 11 and 12, an air release chamber 540 is snapped into the aperture 274 (shown in FIG. 2). Projections 542 (shown in FIG. 12) from the cassette 210 extend part way around the air release chamber 540 to retain the air release chamber securely in the cassette 210. The air release chamber allows gas, such as air, to escape from the blood in the circuit and out of the chamber 540 through a top of the chamber. Optionally, along all of the recesses described herein, projections similar to projections 542 extend from the cassette 210 to secure the tubing in place.

Capsules 544 that allow pressure to be sensed can be positioned in apertures 252 and 254 (shown in FIG. 2). A suitable capsule can include a thin membrane on one side through which pressure in the capsule can be determined, such as by a transducer. The cassette can be arranged so that the thin membrane is placed in close proximity to or in contact with the transducer in the dialysis machine. Suitable capsules are described further in U.S. Pat. No. 5,614,677, "Diaphragm gage for measuring the pressure of a fluid", which is incorporated herein by reference.

In addition to the tubing shown in FIGS. 11 and 12, additional tubing is captured and held in place by the cassette 210, as shown in FIGS. 2 and 16. An arterial tubing line 620 is secured by recess 212. Optionally, along the arterial tubing 620 is an injection site 701 which provides needle or needleless access to the arterial tubing 620. Additionally, a blood volume monitor 704, such as an acoustic cuvette, e.g., blood volume monitor cuvette available from Fresenius Medical Care (Bad Homburg, Germany), can be in line with the arterial tubing 620. At the end of the arterial tubing 620 can be a low force clamp 710, a luer rotating lock 712 and a luer lock recirculation connector 714.

If the arterial tubing 620 includes a capsule 544 at which pressure in the arterial tubing 620 can be sensed, this is retained in aperture 252 of the cassette 210. The arterial tubing 620 extends along recess 218 to a first pump loop adaptor 570, which connects the arterial tubing 620 to one end of the pump loop 575.

As described above, the other end of the pump loop 575 is connected to a second pump loop adaptor 570, which then is in fluid connection with tubing 550, tube adaptor 500a, and an entry port 412 of dialyzer 400 (not shown in FIGS. 7 and 16). If a dialyzer is not connected to the tubing 550, an end connector cap 745 can be on the end of tubing 550 to protect the tubing from being contaminated prior to connection to the dialyzer.

The exit port 413 (shown in FIG. 7) of the dialyzer 400 is connected to another tube adaptor, which connects the dialyzer 400 to dialyzer exit tubing 640. The dialyzer exit tubing 640 is retained by recess 222. If there is no dialyzer in the circuit, e.g., when the circuit is packaged for shipping, the dialyzer exit tubing 640 has an end connector cap 750 for keeping the tubing clean.

Optionally, a capsule 544 for sensing the pressure after the blood exits the dialyzer can be positioned along the dialyzer exit tubing 640 and before the air release chamber 540. The air release chamber 540 includes both an entry port and an exit port. In some embodiments, the capsule 544 leads directly into entry port of the air release chamber 540 with no tubing therebetween. In other embodiments, a short piece of tubing connects capsule 544 with air release chamber 540. Venous tubing 581 extends from the air release chamber 540 exit port and is retained by recess 230. The venous tubing 581 extends past aperture 276 and is retained by recess 235. From the cassette, the tubing 581 leads to a patient when the patient is connected to the hemodialysis machine. Venous tubing 581 can have a luer lock recirculation connector 752 on the end, as well as a luer lock 754 and a clamp 757 are on the venous tubing 581. Optionally, an injection site 758 is also on the venous tubing 581.

Still referring to FIG. 16, in addition to the main circuit tubing described above, additional tubes 720, 724 can be included in the circuit for introducing drugs, such as heparin, or priming solution, such as saline, into the circuit. These tubes can be captured by recesses 241 and 243 (shown in FIG. 3) and can connect to the pump loop adaptors 570. The saline tubing 720 and heparin tubing 724 can be connected to the first and second pump loop adaptors 570. One or more clamps 726 can be on each of the saline tubing 720 and the heparin tubing 724. The saline tubing can also include luer locks 730, 731, 732, 733 and a priming spike 740 on the end of the tubing. The leur locks 730, 731, 732, 733 can allow for disconnecting the tubing at various times during the procedure and flushing fluids from the circuit, such as for routing blood back into the patient at the end of the procedure.

In some embodiments, the saline tubing 720 connects with the pump loop 575 prior to the pump and the heparin tubing 724 connects to the circuit after the pump. The end of the saline tubing 720 and heparin tubing 724 can be snapped into the cassette and held in place by traps 300 and 305 and J-hook 310.

In some embodiments, one or more of the recesses and apertures include projections 261 (FIGS. 4 and 6), which form traps for each of the components, including capsule 544, chamber 540, pump loop adaptors 570, as well as for tubing.

While the cassette has been described as being configured so that a dialyzer can be snapped into and retained by the cassette, other arrangements are possible. The cassette 210 illustrated in FIG. 16, for example, is configured so that the dialyzer can be positioned to merely hang in the cassette 210.

Referring to FIGS. 17A and 17B, the cassette 210 with all of the components and tubing appropriately coiled can be neatly folded into a compact low profile configuration as shown that keeps all of the tubes from tangling. In addition, a rinse bag 790 can be folded below the cassette, for use in rinsing a priming solution through the circuit prior to introducing blood into the circuit. Port caps 793 can be included with the cassette for capping the dialyzer ports 412, 413 after patient treatment and preventing leaking. The cassette 210 and various components, such as the dialyzer 400, tubing port caps 793 and rinse bag 790 can be retained by a tray 794. In embodiments, the tray 794 has molded features that approximate the shape of the components for securely holding the cassette and components. In some embodiments, the tray includes a lid 795. The lid 795 can be on the tray 794 at an angle that allows for accommodation of the dialyzer 400, but that slopes downwardly and close to the pump loop 575. A second tray 794 and lid 795 can be placed upside down on a first tray 794 and lid 795, with the filter 400 held by the first tray 794 close to the pump loop 575 held by the second tray 794 in a mating or clam shell configuration so that the resulting two packaged cassettes form a rectangular box shaped unit. This enables compact packaging of two sets of captured circuitry. In some embodiments, one or more components, such as the dialyzer or the port caps, are not packaged with the cassette and tubing.

The tubing, including the arterial tubing and venous tubing, can be a 0.168 inch inner diameter and a 0.265 inch outer diameter flexible PVC tubing. Other sizes and materials can also be used. The pump loop can be formed from a different size tubing, such as flexible tubing with a 0.315 inch inner diameter and a 0.265 inch outer diameter, which can be formed of PVC. Some of the tubing, such as the tubing leading to the priming solution, is of a smaller size, such as 0.110 inch inner diameter and 0.165 inch outer diameter.

Although the cassette 210 described herein has been referred to as a cassette, the cassette is actually a capture device that captures the tubing and components used in a hemodialysis circuit. In some embodiments, the cassette 210 has tubing integrated therein and optionally has the components integrated therein as well, thereby forming an integrated cassette. In such embodiments, the cassette can be used without additional tubing. Such an integrated cassette can include regions with a membrane through which a sensor on the hemodialysis machine can monitor the fluid in the integrated cassette.

The components that contact the blood are formed from a material suitable for medical devices, that is, a medical grade material. Plastics, such as polyvinylchloride, polycarbonate, polyolefins, polypropylene, polyethylene or other suitable medical grade plastic can be used because of their ease of manufacturing, ready availability and disposable nature. The tubing is constructed from a polymer that is flexible and suitable for medical use, such as an elastomer, including silicon elastomers, or PVC. Other suitable materials include high and low density polyethylene, polypropylene, such as high or low density polypropylene, separately co-extruded mono layers or multiple layers of polyamides, nylons, silicones or other materials commonly known in the art for flexible applications. The portions that do not contact any blood, such as the cassette, can be formed from any rigid semi-flexible molded material that will not break when a small amount of pressure is applied to the material that causes the material to bend. Suitable materials for the cassette are plastics, such as the ones that are described above. If the cassette is an integrated cassette, the cassette is formed of a medical grade material.

Referring to FIG. 18, the cassette is configured to fit into a hemodialysis machine which has a door 600 hinged to the front of the dialysis machine. The door 600 closes onto the cassette to hold the cassette in place. The door 600 closes against machine main body 605. In some embodiments, a portion 610 of the door 600 is transparent, which allows a user to view components held by the cassette, such as the air release chamber. The door 600 can be supported by one or more hinges 615, which allow the door to open to an angle of at least 90°, such as 135° and to close flat against and parallel to the machine main body 605.

The door includes one or more spring loaded pressure disks 620 which apply pressure onto the capsules 544. When the door is closed, the pressure disks 620 press the respective capsules 544 firmly against respective pressure transducers in the machine main body 605. The pressure disks 620 are self aligning and help to ensure that the chambers sit properly on the pressure sensors 685. The bosses 253 (shown in FIG. 4) around capsules 544 (shown in FIG. 12), in some embodiments, also surround pressure sensors 685. Additionally, a projection 630 on the door can be configured to hold tubing in the cassette, such as venous tubing 581, against a sensor in the machine main body 605. In some embodiments, the sensor is an optical sensor. Below the projection 630 is a recess 627 in the door. Recess 627 accommodates the end pieces 273 which project from the front of the cassette 210 and retain the arterial tubing, venous tubing and dialyzer exit tubing.

While the pressure disks 620 have been described above as being spring loaded, other loading mechanisms can be used. For example, the pressure disks can alternatively or additionally be hydraulically or pneumatically driven.

In some embodiments, the door includes one or more features that press the chamber against the main body. Ridge 750 can hold the main body of the air release chamber against the machine body, which holds the main body closer to a level detector, described further below. Post 755 can hold the bottom portion of the chamber, and in some cases the widest portion of the chamber, against the machine body. In some embodiments, the ridge 750 is replaced by a spring loaded projection.

The door 600 can be secured in the closed position by a locking mechanism, such as J-shaped hook 640 (see also FIG. 22). Other suitable locking mechanism include magnets, twisting locks, screw type closures or other locking devices. Referring to FIG. 19, on an exterior of the door is a lever that controls the locking mechanism. On an opposite side of the J-shaped hook 640 is a lever 645 on the outside of the door 600. When the lever 645 is in the down position and flush against the door 600, the J-shaped hook 640 is in its highest vertical position and engages a cross bar 655 (shown in FIG. 18) on the machine main body 605. When the lever 645 is in an extended position (shown in FIG. 21), the J-shaped hook 640 is in its lowest vertical position and disengages the cross bar 655. A depression 650 in the lever 645 guides the user as to where to place pressure on the lever 645 to put the lever 645 into its down position. The lever 645 can extend to a bottom of the door, providing a location for the user to grab the lever 645 so that the lever 645 can be lifted and the door 600 can be opened. When the door 600 is closed, the door 600 is held tightly against the machine main body 605 to ensure that the cassette cannot be released from the body 605 and that the sensors in the body 605 have sufficient proximity or contact with the cassette to be able to obtain accurate readings.

Referring to FIG. 20, the dialysis machine main body 605 includes a pump 670 and a recessed area 675 where the cassette 210 is seated while in the machine. The pump 670 rotates in both a clockwise and counterwise direction. As the pump rotates in one direction, such as clockwise, a feeder section 760, which is shown as a cleavage in a side of the pump face, automatically threads the pump loop to load pump loop onto the pump. When the pump reverses, the pump loop stays loaded in the pump. To remove the pump loop from the pump 670, a pin 720, such as a solenoid driven pin, along a recess in which the pump loop is located extends and pushes the pump loop away from the body of the machine. Reversing the pump direction while the pin 720 is in the extended position forces the pump loop out of the pump face so that the loop is no longer threaded or loaded in the pump 670.

The recessed area 675 can include additional recessed portions 680 to accommodate protruding components held by the cassette 210, such as the air release chamber 540. The recessed area 675 also includes pressure sensors (e.g., pressure transducers) 685 corresponding to the location of the capsules 544 in the cassette 210 and the pressure disks 620. The sensors 685 are fixed in the machine body and are not configured to move. In addition, a sensor assembly 690 is positioned below the pressure sensors 685, so that the blood returning to the patient can be monitored for air bubbles.

The sensor assembly 690 includes two vertical parallel structures 730, 735 with a slot therebetween. The outlet tubing from the chamber fits between the structures 730, 735. A structure 740 is below the parallel structures 730, 735. The sensor assembly 690 measures the blood temperature in the venous line to the patent, as well as in the arterial line. In some embodiments, the blood temperature monitoring portion of the sensor assembly 690 includes an infrared (IR) sensor. Alternatively, or in addition, the sensor assembly 690 includes an ultrasound sensor for measuring blood flow volume. In some embodiments, the sensor assembly 690 includes an air bubble detector. Suitable sensors are provided by Cosense, Inc. (Hauppauge, N.Y.).

A level detector 710 is on the machine body. When the cassette is held by the body, the level detector 710 is adjacent to the air release chamber and can determine whether sufficient priming fluid has been introduced into the chamber to be able to proceed with patient treatment. In some embodiments, the cassette 210 is formed of a sufficiently flexible material that when pressure is placed on the chamber, the cassette allows the chamber to move into direct contact with the level detector 710 to facilitate level sensing.

In some embodiments, the main body 650 of the dialysis machine includes a clamp that can be used to clamp the venous line 581 extending from the cassette 210. The venous clamp can, for example, be positioned on a region of the main body 650 that is adjacent to the aperture 276 (shown in FIG. 2) of the cassette 210 and is aligned with the portion of the venous line extending along the aperture 276. In such embodiments, the aperture 276 allows the venous clamp to receive the venous line to prevent blood flow through the venous line.

When a user is ready to load the hemodialysis machine with a new cassette, the user removes the cassette from the packaging. The cassette has all of the components and tubing that the user requires attached. In some embodiments, the dialyzer is not attached and the user must remove any end caps from the tubes that connect to the dialyzer and connect the dialyzer to the tubes and fit the dialyzer into the cassette. In addition, in some embodiments a waste bag is included with the cassette kit, which can be attached to and one or both of the arterial line or venous line for priming the system. Alternatively, a container can be used to collect spend fluid.

The user opens the door on the machine. The user then places the cassette with the front of the cassette, that is the side with the dialyzer fully exposed facing away from the machine (and toward the user if the user is in front of the machine). The dialyzer is placed to the side of the machine and the recessed portion of the cassette, which holds the air release chamber and most of the tubing, is placed in front of the machine. The guides on the back of the cassette are placed against the side of the machine. Optionally, two stationary dialysate fluid lines (not shown) automatically snap into the dialyzer to provide a dialysis fluid circuit. In some embodiments, the fittings on the back of the dialyzer provide a fluid connection to the interior dialyzer and the dialysate fluid lines connect into the fittings.

As the user places the cassette against the machine body, the recessed portion of the cassette fits into the recessed portion on the front of the machine. Because the recessed portion of the cassette has the same dimensions as at least part of the recessed portion on the front of the machine, the sensors on the machine and components on the cassette are properly aligned. Ridges on the cassette body interact with the machine body, the recessed portion 280 of the cassette seats in the recess 675 in the machine body, the recess 680 behind the air release chamber 540 holds part of the air release chamber 540, the sensor assembly 690 holds tubing 581, and the guides 290, 292 along the back of the cassette 210 hold the cassette 210 against the machine body. One of more of these interactions between the captured components, the cassette and machine body hold the cassette in place. Thus, even with the door open, the cassette and all of the components are held by the machine, even without the user holding the cassette against the machine. Therefore, the user can close the machine door with one hand. The user then closes the door and engages the locking mechanism.

While the dialysis machine described above includes a peristaltic pump, the cassette 210 can alternatively or additionally be configured for use with dialysis machines that use different types of fluid pumps. In some embodiments, for example, the cassette includes tubing that can be connected to an inlet of a fluid pump and tubing that can be connected to an outlet of the fluid pump to allow the pump to pump blood through the cassette and components retained therein.

While capsules 544 have been described as being positioned within apertures 252, 254 in embodiments above to detect pressure, other types of sensor can alternatively or additionally be used. In certain embodiments, for example, sensors that connect directly to the tubing can be positioned within apertures 252, 254.

While the cassette 210 has been described as having a particular pattern of recesses and apertures to receive tubing and other dialysis components, other patterns are possible. For example, the cassette could include additional recesses and apertures to permit additional tubing and components to be retained therein.

While the recesses of the cassette that receive tubing have been described as having a semicircular profile, the recesses can have any profile that enables the cassette to adequately retain the tubing.

Other embodiments are within the scope of the following claims.

What is claimed is:

1. A device for retaining hemodialysis circuit components, the device comprising:
a body having a first portion recessed relative to the plane of a substantially flat second portion adjacent to the first portion, the first portion having a plurality of recesses configured to retain tubes and a first aperture that intersects at least one of the recesses, the second portion having a first slot along a top edge of the second portion and a second slot along a side edge of the second portion, the first and second slots being configured to receive and retain first and second fittings, respectively, of a dialyzer to hold the dialyzer in a substantially fixed position relative to the body,
wherein the device is configured so that the device can be disposed between a door and a main body of a dialysis machine when the door is closed.

2. The device of claim 1, wherein the at least one of the recesses intersected by the aperture is a substantially linear recess.

3. The device of claim 1, wherein the first portion of the body is recessed relative to the second portion of the body.

4. The device of claim 1, further comprising at least one guide projecting from a back surface of the body, wherein the guide has a straight wall.

5. The device of claim 4, wherein the straight wall of the guide is adjacent to the first portion of the body.

6. The device of claim 1, wherein the recesses are semicircular recesses.

7. The device of claim 1, wherein two of the recesses are linear recesses, and the device further comprises a second aperture between the two linear recesses.

8. The device of claim 7, wherein:
the first aperture is circular;
the second aperture is rectangular; and
the cassette further comprises an aperture with a tapered region, wherein the aperture with the tapered region is closer to an upper edge of the device, the second aperture is closer to a lower edge of the device and the first aperture is between the second aperture and the aperture with the tapered region.

9. The device of claim 1, further comprising a tube trap on the body.

10. The device of claim 9, further comprising a hook configured to position a tube on the body.

11. The device of claim 1, further comprising a slot extending from an edge of the device into the first portion.

12. The device of claim 1, further comprising a tubing lock adjacent to at least one of the plurality of recesses.

13. The device of claim 12, wherein the tubing lock comprises two adjacent projections.

14. The device of claim 1, further comprising:
a second aperture;
a crossbar that extends across the second aperture; and
a chamber lock adjacent to the crossbar.

15. The device of claim 14, wherein the second aperture includes a portion with two parallel walls and a tapered portion.

16. The device of claim 15, wherein adjacent to the second aperture is a stabilizer that extends parallel to the crossbar and to opposite sides of the first portion of the body.

17. An assembly comprising:
the device of claim 1; and
a dialyzer held by the slot along the top edge of the second portion of the body and by the slot along the side edge of the second portion of the body.

18. The assembly of claim 17, wherein the dialyzer includes a fitting, the fitting including a tab that engages the body to lock the dialyzer against the body.

19. An assembly comprising:
the device of claim 1, wherein the body forms a loop adaptor recess and the portion of the body forming the loop adaptor recess has an aperture; and
a loop adaptor disposed in the loop adaptor recess, wherein the loop adaptor includes a locking pin disposed in the aperture in the portion of the body forming the loop adaptor recess.

20. The assembly of claim 19, wherein:
the device includes a trap adjacent to the loop adaptor recess; and
the loop adaptor is held by the trap.

21. The assembly of claim 19, further comprising:
a plurality of tubes, wherein each tube is in a recess of the plurality of recesses;
a capsule in fluid communication with a tube of the plurality of tubes; and
an air release chamber in fluid communication with a tube of the plurality of tubes.

22. The assembly of claim 21, further comprising a dialyzer in fluid communication with a tube of the plurality of tubes.

23. The device of claim 1, wherein the slots are configured so that, when the first and second fittings of the dialyzer are disposed in the slots during use, the dialyzer hangs from the body.

24. The device of claim 1, wherein the slots are configured so that, when the first and second fittings of a dialyzer are disposed in the slots during use, the dialyzer is positioned parallel to a vertical axis of the body.

25. The device of claim 1, wherein the first slot is a substantially U-shaped slot.

26. The device of claim 25, wherein the second slot is a substantially U-shaped slot.

27. The device of claim 1, wherein the slots are configured so that, with the first fitting of the dialyzer disposed in the first slot, the second fitting of the dialyzer can be inserted into the second slot by rotating the dialyzer about the first fitting.

28. A hemodialysis circuit component kit, comprising:
a cassette including:
a body having a first portion and a second portion adjacent to the first portion, the first portion having a plurality of recesses configured to retain tubes, wherein a first aperture intersects at least one of the recesses, the second portion having a first slot along a top edge of the second portion and a second slot along a side edge of the second portion, the first and second slots being arranged to allow the body to capture a dialyzer, and the first portion of the body forms a loop adaptor recess and a second aperture in a region of the first portion of the body that forms the loop adaptor recess;
a loop adaptor in the loop adaptor recess of the body, wherein the loop adaptor includes a locking pin disposed in the second aperture;
a plurality of tubes, wherein each tube is in a recess of the plurality of recesses;
a capsule in fluid communication with a tube of the plurality of tubes; and
an air release chamber in fluid communication with a tube of the plurality of tubes.

29. The kit of claim 28, further comprising a dialyzer in fluid communication with a tube of the plurality of tubes.

30. The kit of claim 29, further comprising a port caps, wherein the port caps are sized to fit onto end ports of the dialyzer.

31. The kit of claim 28, further comprising a waste bag, wherein a waste bag can be connected to a tube of the plurality of tubes.

32. A device for retaining hemodialysis components, the device comprising:
a body having a first portion recessed relative to the plane of a substantially flat second portion adjacent to the first portion, the first portion forming a recessed region and an aperture that intersects the recessed region, the recessed region being configured to retain a blood line, the aperture being configured to receive a hemodialysis component that is in fluid communication with the blood line, the second portion of the body further forming first and second slots configured to receive and retain first and second fittings, respectively, of a dialyzer to hold the dialyzer in a substantially fixed position relative to the body,
wherein the body, the blood line, and the hemodialysis component are configured to be disposed between a main body and a door of a hemodialysis machine.

33. The device of claim 32, wherein the hemodialysis component is an air release chamber.

34. The device of claim 32, wherein the hemodialysis component is a capsule with a flexible membrane.

35. The device of claim 32, wherein the slots are configured so that, when the first and second fittings of the dialyzer are disposed in the slots during use, the dialyzer hangs from the body.

36. The device of claim 32, wherein the slots are configured so that, when the first and second fittings of the dialyzer are disposed in the slots during use, the dialyzer is positioned parallel to a vertical axis of the body.

37. The device of claim 32, wherein the first slot is a substantially U-shaped slot.

38. The device of claim 37, wherein the second slot is a substantially U-shaped slot.

39. The device of claim 32, wherein the slots are configured so that, with the first fitting of the dialyzer disposed in the first slot, the second fitting of the dialyzer can be inserted into the second slot by rotating the dialyzer about the first fitting.

40. An assembly comprising:
device for retaining hemodialysis circuit components, the device comprising a body having a first portion and a second portion adjacent to the first portion, the first portion having a plurality of recesses configured to retain tubes and a first aperture that intersects at least one of the recesses, the second portion having a first slot along a top edge of the second portion and a second slot along a side edge of the second portion; and a dialyzer held by the slot along the top edge of the second portion of the body and by the slot along the side edge of the second portion of the body.

41. The assembly of claim 40, wherein the dialyzer includes a fitting, the fitting including a tab that engages the body to lock the dialyzer against the body.

42. The assembly of claim 40, wherein the body forms a loop adaptor recess and the portion of the body forming the loop adaptor recess has an aperture, and the assembly further comprises a loop adaptor disposed in the loop adaptor recess, wherein the loop adaptor includes a locking pin disposed in the aperture in the portion of the body forming the loop adaptor recess.

43. The assembly of claim 42, wherein the device includes a trap adjacent to the loop adaptor recess, and the loop adaptor is held by the trap.

44. The assembly of claim 42, further comprising:
a plurality of tubes, wherein each tube is in a recess of the plurality of recesses;
a capsule in fluid communication with a tube of the plurality of tubes; and
an air release chamber in fluid communication with a tube of the plurality of tubes.

45. The assembly of claim 44, wherein the dialyzer is in fluid communication with a tube of the plurality of tubes.

46. A device for retaining hemodialysis circuit components, the device comprising:
a body having a first portion recessed relative to the plane of a substantially flat second portion adjacent to the first portion, the first portion having a plurality of semicircular recesses configured to retain tubes and a first aperture that intersects at least one of the recesses, the second portion having a first slot along a top edge of the second portion and a second slot along a side edge of the second portion, the first and second slots being configured to receive and retain first and second fittings, respectively, of a dialyzer to hold the dialyzer in a substantially fixed position relative to the body.

47. A device for retaining hemodialysis circuit components, the device comprising:
a body having a first portion recessed relative to the plane of a substantially flat second portion adjacent to the first portion, the first portion having a plurality of recesses configured to retain tubes and a first aperture that intersects at least one of the recesses, the second portion having a first slot along a top edge of the second portion and a second slot along a side edge of the second portion, the first and second slots being configured to receive and retain first and second fittings, respectively, of a dialyzer to hold the dialyzer in a substantially fixed position relative to the body,
wherein the slots are configured so that, with the first fitting of the dialyzer disposed in the first slot, the second fitting of the dialyzer can be inserted into the second slot by rotating the dialyzer about the first fitting.

48. A device for retaining hemodialysis circuit components, the device comprising:
a body having a first portion recessed relative to the plane of a substantially flat second portion adjacent to the first portion, the first portion having a plurality of recesses configured to retain tubes and a first aperture that intersects at least one of the recesses, the second portion having a first slot along a top edge of the second portion and a second slot along a side edge of the second portion, the first and second slots being configured to receive and retain first and second fittings, respectively, of a dialyzer to hold the dialyzer in a substantially fixed position relative to the body,
wherein the slots are configured so that, with the first fitting of the dialyzer disposed in the first slot, the second fitting of the dialyzer can be inserted into the second slot by rotating the dialyzer about the first fitting.

* * * * *

UNITED STATES PATENT AND TRADEMARK OFFICE
CERTIFICATE OF CORRECTION

| | | |
|---|---|---|
| PATENT NO. | : 8,110,104 B2 | Page 1 of 1 |
| APPLICATION NO. | : 12/234186 | |
| DATED | : February 7, 2012 | |
| INVENTOR(S) | : Martin Joseph Crnkovich et al. | |

It is certified that error appears in the above-identified patent and that said Letters Patent is hereby corrected as shown below:

On the Title Page
Item (75) (inventors), line 6:
    delete "Rancho Sante Fe," and replace with --Rancho Santa Fe,--.

Signed and Sealed this
Tenth Day of April, 2012

David J. Kappos
*Director of the United States Patent and Trademark Office*